(12) United States Patent
Tanifum et al.

(10) Patent No.: US 11,116,854 B2
(45) Date of Patent: Sep. 14, 2021

(54) TARGETED CONTRAST AGENTS FOR MRI OF AMYLOID DEPOSITION

(71) Applicant: Texas Children's Hospital, Houston, TX (US)

(72) Inventors: Eric A. Tanifum, Richmond, TX (US); Ketankumar B. Ghaghada, Sugar Land, TX (US); Ananth V. Annapragada, Manvel, TX (US)

(73) Assignee: Texas Children's Hospital, Houston, TX (US)

( * ) Notice: Subject to any disclaimer, the term of this patent is extended or adjusted under 35 U.S.C. 154(b) by 0 days.

(21) Appl. No.: 17/162,126

(22) Filed: Jan. 29, 2021

(65) Prior Publication Data

US 2021/0236662 A1     Aug. 5, 2021

Related U.S. Application Data

(60) Provisional application No. 62/967,295, filed on Jan. 29, 2020.

(51) Int. Cl.
*A61K 49/18* (2006.01)
*A61K 47/24* (2006.01)
*A61K 49/10* (2006.01)

(52) U.S. Cl.
CPC .......... *A61K 49/1812* (2013.01); *A61K 47/24* (2013.01); *A61K 49/108* (2013.01)

(58) Field of Classification Search
CPC .................. C07F 5/003; A61K 49/126; A61K 49/1812; A61K 49/085; A61K 49/10
See application file for complete search history.

(56) References Cited

U.S. PATENT DOCUMENTS

| | | | |
|---|---|---|---|
| 2014/0227175 A1 | 8/2014 | Vasiljeva et al. | |
| 2015/0023875 A1 | 1/2015 | Farokhzad et al. | |
| 2016/0101197 A1* | 4/2016 | Annapragada | A61K 49/1812 424/9.321 |
| 2017/0080111 A1 | 3/2017 | Annapragada et al. | |
| 2019/0255196 A1* | 8/2019 | Annapragada | C07F 5/003 |

FOREIGN PATENT DOCUMENTS

WO    2018201069    11/2018

OTHER PUBLICATIONS

De Vries et al., Contrast Media Mol. Imaging 2014,9, 83-91. (Year: 2014).*
Tanifum et al., Journal of Alzheimer's Disease 52 (2016) 731-745 (Year: 2016).*
Tanifum et al., Journal of Alzheimer's Disease 52 (2016) 731-745, Supplemental Materials (Year: 2016).*
Badachhape, et al. Pre-clinical dose-ranging efficacy, pharmacokinetics, tissue biodistribution, and toxicity of a targeted contrast agent for MRI of amyloid deposition in Alzheimer's disease, Scientific Reports, Sep. 30, 2020, vol. 10, p. 1-10.
International Search Report and Written Opinion issued in PCT/US2021/015683, dated Apr. 13, 2021.

* cited by examiner

*Primary Examiner* — Michael G. Hartley
*Assistant Examiner* — Leah H Schlientz
(74) *Attorney, Agent, or Firm* — Kern Kendrick, LLC; Benjamen E. Kern

(57) ABSTRACT

A liposomal composition ("ADx-001") is provided, ADx-001 comprising a first phospholipid; a sterically bulky excipient that is capable of stabilizing the liposomal composition; a second phospholipid that is derivatized with a first polymer; a macrocyclic gadolinium-based imaging agent; and a third phospholipid that is derivatized with a second polymer, the second polymer being conjugated to a targeting ligand. The macrocyclic gadolinium-based imaging agent may be conjugated to a fourth phospholipid.

18 Claims, 15 Drawing Sheets

TARGETED CONTRAST AGENTS FOR MRI OF AMYLOID DEPOSITION

CROSS-REFERENCE TO RELATED APPLICATIONS

This application claims priority from U.S. Provisional Patent Application No. 62/967,295, filed on Jan. 29, 2020, which is incorporated by reference herein in its entirety.

STATEMENT REGARDING FEDERALLY SPONSORED RESEARCH OR DEVELOPMENT

This invention was made with U.S. Government support under Contract Nos. R44AG051292, U01DE028233, and R01HD094347 awarded by the National Institutes of Health. The U.S. Government has certain rights in the invention.

BACKGROUND

A definitive diagnosis of Alzheimer's disease ("AD") requires postmortem neuropathological demonstration of β-amyloid plaques and neurofibrillary tau tangles. However, advances in the development of position emission tomography ("PET") imaging probes for these biomarkers have facilitated a new research framework to study and characterize the disease in vivo. Although not approved for clinical diagnosis, this framework, advanced by the National Institute of Aging and Alzheimer's Associated, defines biological AD by either in vivo PET imaging or other biomarker evidence of β-amyloid plaques and neurofibrillary tau tangles. The use of targeted PET tracers in clinical research has dramatically improved understanding of the evolution of AD biomarkers in the context of dementia. The clinical deployment of such non-invasive imaging AD biomarkers may enable early diagnosis of AD-related dementia and facilitate early intervention.

The build-up of β-amyloid plaques in the brain is one of the earliest pathogenic events in AD. Pre-clinical and clinical studies using PET probes have demonstrated that parenchymal deposition of amyloid plaques begins decades before clinical presentation of cognitive impairment in AD-related dementia. Furthermore, the formation of amyloid plaques has been causally linked to the pathogenesis of neurofibrillary tau tangles. Although amyloid imaging PET probes, such as 18F-florbetaben, 18F-florbetapir, and 18F-flutemetamol have substantially advanced understanding of AD pathophysiology leading to cognitive impairment and are playing a critical role in clinical trials for the evaluation of disease-modifying investigational therapies, accessibility to PET modalities for the general population remains a worldwide problem. An amyloid imaging agent for use with magnetic resonance imaging ("MRI") could be transformative due to ease of accessibility and comparatively low cost.

A high T1 relaxivity, amyloid-targeted liposomal-gadolinium (Gd) nanoparticle contrast agent (containing a first linear Gd chelate, Gd-DTPA bis(stearylamide) ("Gd-DTPA-BSA"), conjugated on the internal and external surfaces of the liposome bilayer, and a second linear Gd chelate, gadobenate dimeglumine ("Gd-BOPTA"), in the core interior of the liposomes) has enabled in vivo MRI of amyloid plaques in transgenic mouse models of AD. See WO2016057812A1 and Ghaghada K B, Ravoori M, Sabapathy D, Bankson J, Kundra V, et al. (2009) New Dual Mode Gadolinium Nanoparticle Contrast Agent for Magnetic Resonance Imaging, PLoS ONE 4(10); e7628 Doi:10.1371/journal.pone. 0007628, each of which is incorporated by reference herein in its entirety. However, evidence has emerged of brain deposition of Gd dissociated from such linear chelates. Thus, a more stable targeted liposomal Gd contrast agent for MRI of amyloid plaques is needed.

SUMMARY

In one aspect, a liposomal composition ("ADx-001") is provided, ADx-001 comprising a first phospholipid; a sterically bulky excipient that is capable of stabilizing the liposomal composition; a second phospholipid that is derivatized with a first polymer; a macrocyclic gadolinium-based imaging agent; and a third phospholipid that is derivatized with a second polymer, the second polymer being conjugated to a targeting ligand, the targeting ligand being represented by:

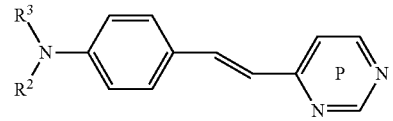

wherein,

Pyrimidine "P" may be substituted with zero, one, or more of —OH, O-alkyl, and —NH$_2$;

$R^2$ is a linking group comprising $C_1$-$C_6$ alkyl or $C_1$-$C_6$ alkoxyalkyl; and $R^3$ is hydrogen, $C_1$-$C_6$ alkyl, or $C_1$-$C_6$ alkoxyalkyl, and $R^3$ other than hydrogen is substituted with zero, one, or more —OH.

In a further aspect, the first phospholipid comprises hydrogenated soy L-α-phosphatidylcholine ("HSPC"); the sterically bulky excipient that is capable of stabilizing the liposomal composition comprises cholesterol ("Chol"); the second phospholipid that is derivatized with a first polymer comprises 1,2-distearoyl-sn-glycero-3-phosphoethanolamine-N-(methoxy (polyethylene glycol)-2000) ("DSPE-mPEG2000"); and the macrocyclic gadolinium-based imaging agent comprises gadolinium(3+) 2-[4,7,10-tris(carboxylatomethyl)-1,4,7,10-tetrazacyclododec-1-yl] acetate ("gadoterate" or "Gd(III)-DOTA") and is conjugated to a fourth phospholipid, e.g.:

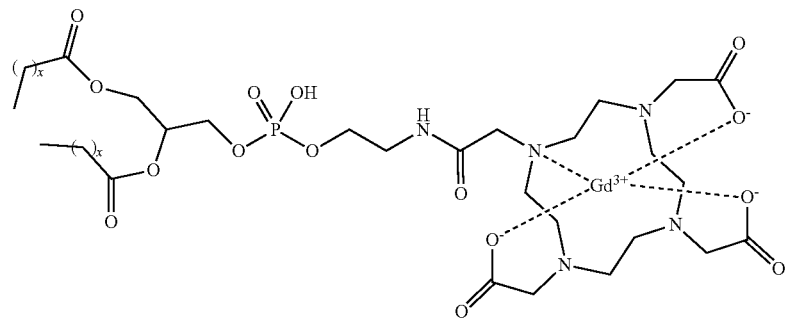

or a salt (e.g., a sodium salt) thereof. In some aspects, the variable x may be one of: 12, 13, 14, 15, 16, 17, or 18. In one aspect, the variable x is 16 (the conjugate: "Gd(III)-DOTA-DSPE"). In some aspects, the third phospholipid that is derivatized with a second polymer, the second polymer being conjugated to the targeting ligand, may comprise:

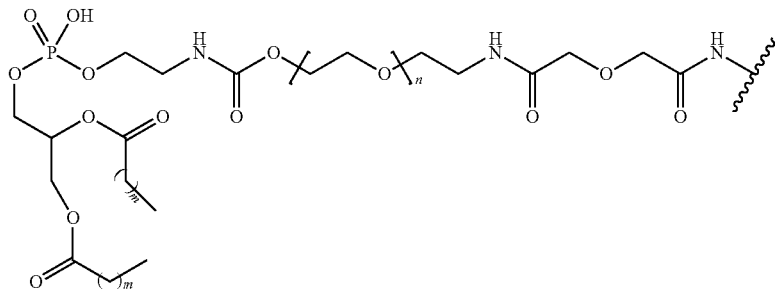

or a salt (e.g., an ammonium phosphate salt) thereof. In some aspects, the variable n may be any integer from about 10 to about 100, for example, about 60 to about 100, about 70 to about 90, about 75 to about 85, about 77, or about 79. The variable m may be one of: 12, 13, 14, 15, 16, 17, or 18. For example, n may be 77, and m may be 14; n may be 79, and m may be 14; n may be 77, and m may be 16; and n may be 79, and m may be 16.

In one aspect, the targeting ligand comprises:

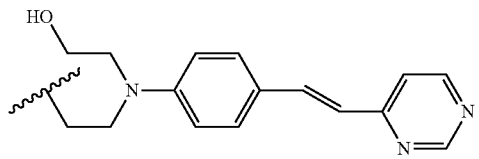 [SMILES: *CCN(CCO)c1ccc(/C=C/c2ccncn2)cc1]

("Compound iii").

In one aspect, n is 79, m is 16 ("DSPE-PEG3500"), and the targeting ligand comprises Compound iii:

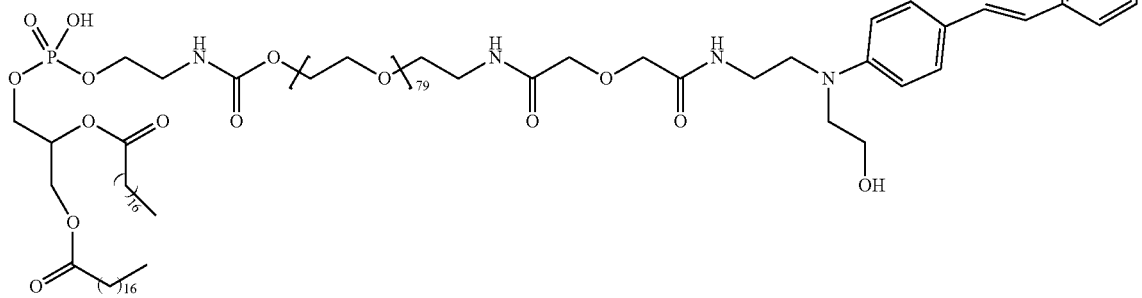

(the conjugate: "ET3-73"), including as a salt (e.g., an ammonium phosphate salt) thereof.

In one aspect, a method for imaging amyloid deposits in a subject is provided. The method may comprise introducing in the subject a detectable quantity of liposomal composition. The method may comprise allowing sufficient time for the liposomal composition to be associated with one or more amyloid deposits. The method may comprise detecting the liposomal composition associated with the one or more amyloid deposits.

In one aspect, the liposomal composition of the method for imaging amyloid deposits in a subject may comprise ADx-001. In one aspect, the liposomal composition of the method for imaging amyloid deposits in a subject may comprise Gd(III)-DOTA-DSPE and ET3-73. In one aspect, the liposomal composition of the method for imaging amyloid deposits in a subject may comprise HSPC, Chol, DSPE-mPEG2000, Gd(III)-DOTA-DSPE, and ET3-73.

In one aspect, the liposomal compositions are suitable for use in imaging amyloid deposits in a patient, the use comprising: introducing into the patient a detectable quantity of the liposomal composition; allowing sufficient time for the liposomal composition to be associated with one or more amyloid deposits; and detecting the liposomal composition associated with the one or more amyloid deposits. In one aspect, the use comprises detecting using MRI.

In one aspect, the use further comprises: identifying the patient as potentially having AD according to detecting the liposomal composition associated with the one or more amyloid deposits; subjecting the patient to an analysis for tau neurofibrillary tangles; and upon determining the presence of tau neurofibrillary tangles in conjunction with detecting the liposomal composition associated with the one or more amyloid deposits, diagnosing the patient with AD.

DETAILED DESCRIPTION

Figure 1:
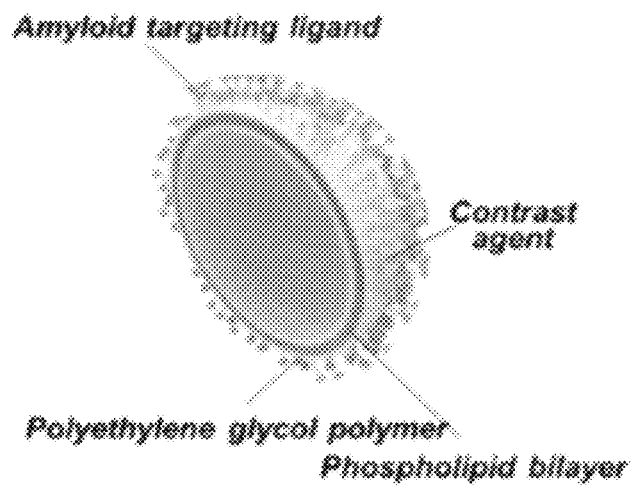
FIG. 1 provides an example cross-sectional depiction of a liposome comprising a targeted contrast agent for MRI of amyloid deposition.
Figure 2:
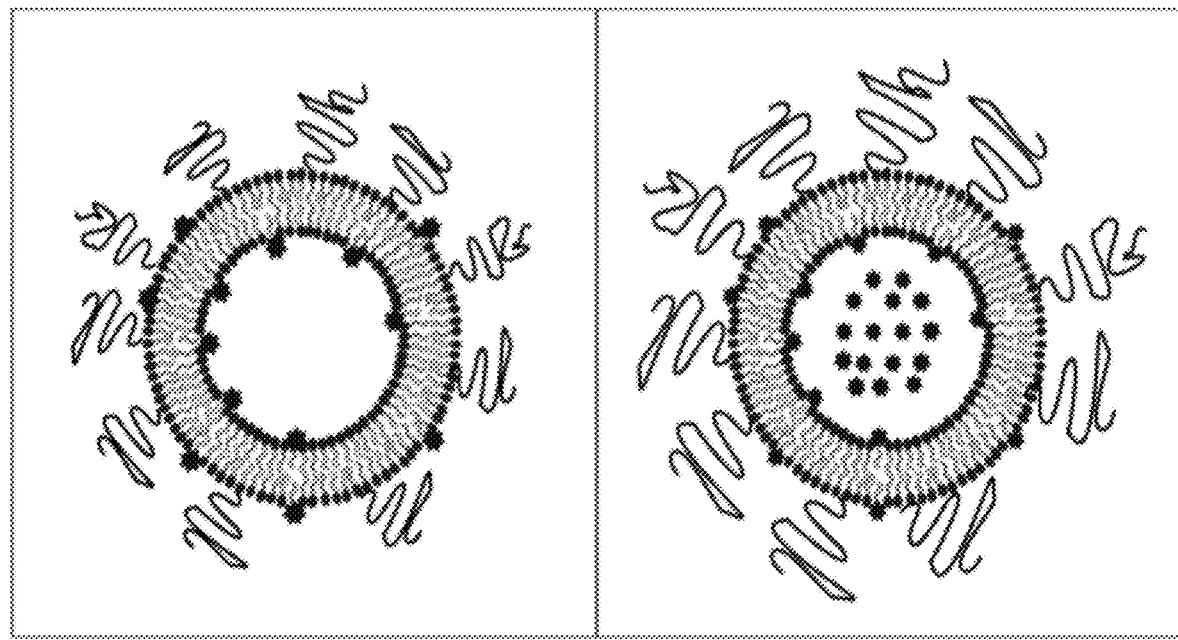
FIG. 2 shows a representative schematic of the surface conjugated macrocyclic Gd-based imaging agent ("SC-Gd") as described herein compared to prior art dual Gd liposomes ("Dual-Gd").

A novel amyloid-targeted liposomal-Gd contrast agent, ADx-001, has been developed based on a highly stable macrocyclic Gd-DOTA imaging moiety. ADx-001 may be generally understood as depicted in cross-section form in FIG. 1. FIG. 2 shows a representative schematic of the conjugation of the macrocyclic gadolinium-based imaging agent as described herein ("SC-Gd"), with the Gd chelates conjugated on the internal and external surfaces of the liposome bilayer, compared to the dual Gd liposomes of WO2016057812A1, which contain both core-encapsulated and surface-conjugated Gd chelates, e.g., as described in WO2016057812A1 and/or in Tanifum E A, Ghaghada K, Vollert C, Head E, Eriksen J L, Annapragada A. A Novel Liposomal Nanoparticle for the Imaging of Amyloid Plaque by Magnetic Resonance Imaging. J Alzheimer's Dis. 2016. doi:10.3233/JAD-151124, each of which is incorporated by reference herein in its entirety.

Figure 3:
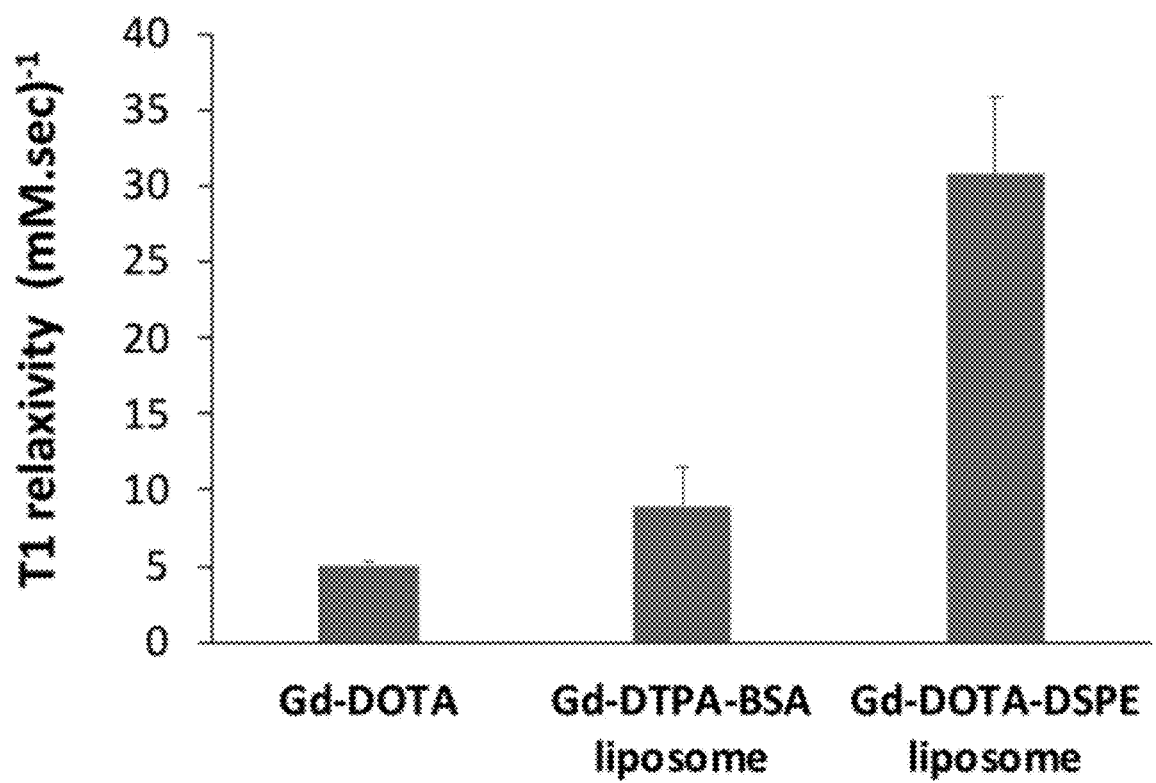
FIG. 3 shows a comparison of $T_1$ relaxivity of Gd(III) forms at 1T field strength between "free" Gd(III)-DOTA (i.e., not conjugated to a liposome), the prior art Gd(III)-DTPA-BSA liposomes, and the Gd(III)-DOTA-DSPE liposomes (i.e., ADx-001 liposomes) as described herein.

Contrast agents with higher $T_1$ relaxivities produce stronger enhancement. FIG. 3 shows a comparison of $T_1$ relaxivity of Gd(III) forms at 1T field strength between "free" Gd(III)-DOTA (i.e., not conjugated to a liposome), the prior art Gd(III)-DTPA-BSA liposomes, and the Gd(III)-DOTA-DSPE liposomes (i.e., ADx-001 liposomes) as described herein. ADx-001 exhibits 3-fold higher $T_1$ relaxivity compared to the prior art Gd(III)-DTPA-BSA liposomes.

More specifically, liposomal Gd-DOTA, with Gd DOTA conjugated to a phospholipid, exhibits approximately three-fold higher T1 relaxivity (~31 mM-1 S-1 on a Gd-basis and ~2,295,000 mM-1 S-1 on a nanoparticle basis at 1 T field strength) than liposomal Gd-DTPA (~9.0 mM-1 S-1 on a Gd-basis and ~668,000 mM-1 S-1 on a nanoparticle basis at 1 T field strength) where Gd-DTPA is conjugated to bis (stearylamide). Gd conjugation is important on at least three bases. First, conjugation of Gd-chelate to a macromolecule slows the rotational correlation of the Gd atom, and therefore increases the rotational correlation time. A higher rotational correlation time yields higher T1 relaxivity. Second, conjugation of Gd-chelate to a phospholipid (here, DSPE) (Gd-DOTA-DSPE) further increases the rotational correlation time compared to Gd-chelate conjugated to bis (stearylamide) (Gd-DTPA-BSA), and therefore Gd-DOTA-DSPE liposomes perform better (higher T1 relaxivity) compared to Gd-DTPA-BSA liposomes. Finally, by conjugating to a true phospholipid, the stability of insertion into the bilayer is greater. In contrast, the lack of the phosphatidyl group in Gd-DTPA-BSA reduces the amphiphilicity of the molecule, and therefore the stability of insertion.

Thus, in one aspect, ADx-001 comprises a first phospholipid; a sterically bulky excipient that is capable of stabilizing the liposomal composition; a second phospholipid that is derivatized with a first polymer; a macrocyclic gadolinium-based imaging agent; and a third phospholipid that is derivatized with a second polymer, the second polymer being conjugated to a targeting ligand. The macrocyclic gadolinium-based imaging agent may be conjugated to a fourth phospholipid.

Phospholipids

In some aspects, suitable phospholipids include those where the two hydrocarbon chains are between about 14 and about 24 carbon atoms in length and have varying degrees of unsaturation. In some aspects, suitable phospholipids include HSPC, 1,2-dipalmitoyl-sn-glycero-3-phosphocholine ("DPPC"), 1,2-distearoyl-sn-glycero-3-phosphocholine ("DSPC"), 1,2-distearoyl-sn-glycero-3-phosphoethanolamine ("DSPE"), and mixtures of two or more thereof. Suitable phospholipids may be naturally occurring or synthetic.

In some aspects, suitable phospholipids may include any of those listed in WO2005107820A1, the content of paragraphs [0031]-[0033] of which is incorporated by reference herein in its entirety.

Polymer-Derivatized Phospholipids

In some aspects, the liposomes of the liposomal composition may include a surface that contains or is coated with flexible water soluble (hydrophilic) polymer chains. These polymer chains may prevent interaction between the liposomes and blood plasma components, the plasma components playing a role in uptake of liposomes by cells of the blood and removal of the liposomes from the blood. The liposomes may avoid uptake by the organs of the mononuclear phagocyte system, primarily the liver and spleen (the reticulendothelial system).

In one aspect, the polymer in the derivatized phospholipid may be polyethylene glycol ("PEG"). The PEG can have any of a variety of molecular weights. In one example, the PEG chain may have a molecular weight between about 1,000-10,000 daltons. Once a liposome is formed, the PEG chains may provide a surface coating of hydrophilic chains sufficient to extend the blood circulation time of the liposomes in the absence of such a coating.

In some aspects, the second phospholipid that is derivatized with a first polymer comprises DSPE-mPEG2000. In some aspects, the third phospholipid that is derivatized with a second polymer, the second polymer being conjugated to the targeting ligand, comprises:

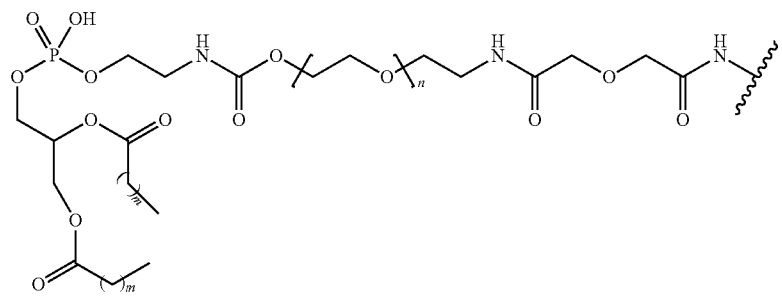

or a salt (e.g., an ammonium phosphate salt) thereof, wherein the variable n may be any integer from about 10 to about 100, for example, about 60 to about 100, about 70 to about 90, about 75 to about 85, about 77, or about 79. The variable m may be one of: 12, 13, 14, 15, 16, 17, or 18. For example, n may be 77, and m may be 14; n may be 79, and m may be 14; n may be 77, and m may be 16; and n may be 79, and m may be 16. In some aspects, the third phospholipid that is derivatized with a second polymer comprises DSPE-PEG3500.

In some aspects, suitable polymers may include any of those listed in WO2005107820A1, the content of paragraphs [0034]-[0038] of which is incorporated by reference herein in its entirety. In some embodiments, the phospholipid derivatized by a polymer may be any of those combinations disclosed in WO2016057812A1.

Sterically Bulky Excipients

In some aspects, the liposomes may include stabilizing excipients. For example, the liposomal compositions may be formulated to comprise Chol. In other aspects, the liposomal compositions may comprise fatty alcohols, fatty acids, cholesterol esters, other pharmaceutically acceptable excipients, and mixtures thereof.

Macrocyclic Gadolinium-Based Imaging Agents

The liposomal composition comprises a macrocyclic Gd-based imaging agent. In some aspects, the macrocyclic gadolinium-based imaging agent comprises Gd(III)-DOTA conjugated to a phospholipid, e.g.:

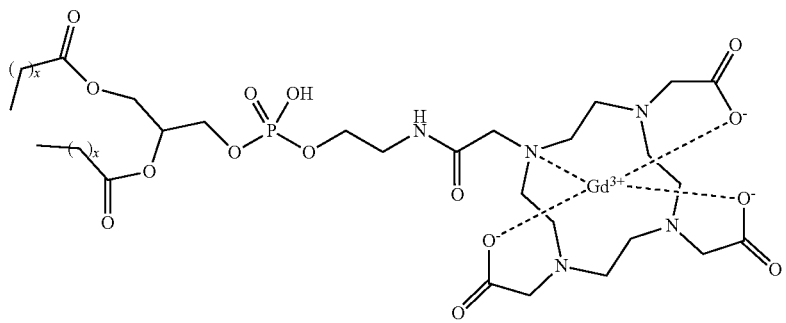

or a salt (e.g., a sodium salt) thereof. In some aspects, the variable x may be one of: 12, 13, 14, 15, 16, 17, or 18. In one aspect, the variable x is 16 and the conjugate is Gd(III)-DOTA-DSPE.

In other aspects, the macrocyclic gadolinium-based imaging agent comprises:

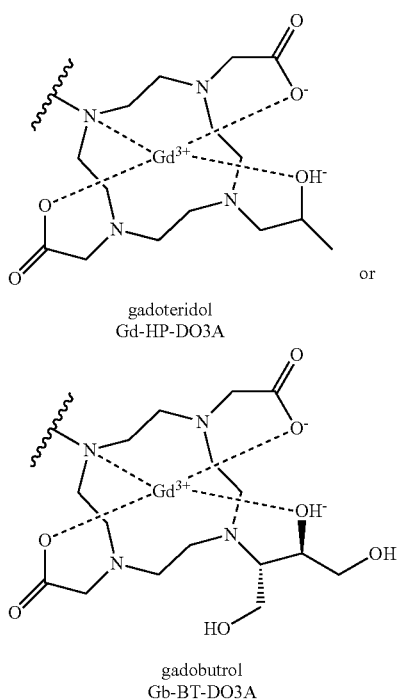

gadoteridol
Gd-HP-DO3A or gadobutrol
Gb-BT-DO3A

Targeting Ligands

The liposome compositions comprise at least one phospholipid that is derivatized with a polymer, the polymer being conjugated to a targeting ligand. Thus, in some aspects, the phospholipid is modified to include a spacer chain. The spacer chain may be a hydrophilic polymer. The hydrophilic polymer may typically be end-functionalized for coupling to the targeting ligand. The functionalized end group may be, for example, a maleimide group, a bromoacetamide group, a disulfide group, an activated ester, or an aldehyde group. Hydrazide groups are reactive toward aldehydes, which may be generated on numerous biologically relevant compounds. Hydrazides may also be acylated by active esters or carbodiimide-activated carboxyl groups. Acyl azide groups reactive as acylating species may be easily obtained from hydrazides and permit the attachment of amino containing ligands.

In some aspects, the targeting ligand may be accessible from the surface of the liposome and may specifically bind or attach to, for example, one or more molecules or antigens. These targeting ligands may direct or target the liposomes to a specific cell or tissue, e.g., an amyloid-β plaque, and may bind to a molecule or antigen on or associated with the cell or tissue.

The targeting ligand is represented by:

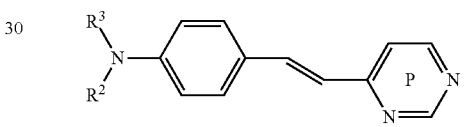

wherein,

Pyrimidine "P" may be substituted with zero, one, or more of —OH, O-alkyl, and —NH$_2$;

$R^2$ is a linking group comprising $C_1$-$C_6$ alkyl or $C_1$-$C_6$ alkoxyalkyl; and $R^3$ is hydrogen, $C_1$-$C_6$ alkyl, or $C_1$-$C_6$ alkoxyalkyl, and $R^3$ other than hydrogen is substituted with zero, one, or more —OH.

In one aspect, the targeting ligand is Compound iii. In one aspect, the phospholipid-polymer-targeting ligand conjugate is ET3-73.

In further aspects, the targeting ligand is any of Compounds i-xiii as disclosed in WO2016057812A1. In yet further aspects, the targeting ligand is Compound ii, iii, xi, and xiii as disclosed in WO2016057812A1.

Liposomes

"Liposomes" generally refer to spherical or roughly spherical particles containing an internal cavity. The walls of liposomes may include a bilayer of lipids. These lipids can be phospholipids. Numerous lipids and/or phospholipids may be used to make liposomes. One example are amphipathic lipids having hydrophobic and polar head group moieties, which may form spontaneously into bilayer vesicles in water, as exemplified by phospholipids, or which may be stably incorporated into lipid bilayers, with their hydrophobic moiety in contact with the interior, hydrophobic region of the bilayer membrane, and their polar head group moiety oriented toward the exterior, polar surface of the membrane. Liposomes may be prepared by any known method, including as described in the Examples herein, in WO2016057812A1, and in WO2012139080A1, which is incorporated by reference herein in its entirety. FIG. 1 provides an example cross-sectional depiction of a liposome comprising a targeted contrast agent for MRI of amyloid deposition.

In one aspect, ADx-001 comprises: HSPC; Chol; DSPE-mPEG2000; ET3-73; and Gd(III)-DOTA-DSPE. In some aspects, the first phospholipid may comprise DPPC, DSPC, or a mixture of DPPC and DSPC. In one aspect, the lipid composition and molar ratio (%) of components in ADx-001 are HSPC:Chol:DSPE-mPEG2000:Gd(III)-DOTA-DSPE:ET3-73=about 31.5:about 40:about 2.5:about 25:about 1. In some aspects, the molar ratio of any one of HSPC:Chol:DSPE-mPEG2000:Gd(III)-DOTA-DSPE:ET3-73 may be adjusted by up to 10%, thus, 31.5±10%:40±10%:2.5±10%:25±10%:1±10%. In one aspect, the lipid composition and molar ratio (%) of components in ADx-001 are HSPC:Chol:DSPE-mPEG2000:Gd(III)-DOTA-DSPE:ET3-73=about 32.5:about 40:about 2:about 25:about 0.5.

In one aspect, the HSPC content in ADx-001 is between about 24 mg/mL and about 32 mg/mL (total lipid). In one aspect, the Chol content in ADx-001 is between about 14 mg/mL and about 19 mg/mL. In one aspect, the DSPE-mPEG2000 content in ADx-001 is between about 5 mg/mL and about 7 mg/mL. In one aspect, the Gd(III)-DOTA-DSPE content in ADx-001 is between 30 mg/mL and 45 mg/mL. In one aspect, the ET3-73 content in ADx-001 is between about 2 mg/mL and about 3 mg/mL. In one aspect, the free gadolinium content in ADx-001 is ≤100 µg/mL, including <2.5 µg/mL.

In one aspect, the liposomal composition has a pH of between 6.4 and 8.4. In a further aspect, the liposomes have an osmolality of between 200-400 mOsmol/kg. In a further aspect, the liposomes have vesicle size (Z-average) as measured by dynamic light scattering of less than 200 nm ($D_{50}$), including less than 150 nm ($D_{50}$), including about 140 nm ($D_{50}$), and including about 120 nm ($D_{50}$).

The term "about" in conjunction with a number is intended to include 10% of the number. This is true whether "about" is modifying a stand-alone number or modifying a number at either or both ends of a range of numbers. In other words, "about 10" means from 9 to 11. Likewise, "about 10 to about 20" contemplates 9 to 22 and 11 to 18. In the absence of the term "about," the exact number is intended. In other words, "10" means 10.

EXAMPLES

Dose-response, pharmacokinetics, and biodistribution in animal models of ADx-001 were studied. Dose-ranging efficacy studies were performed in a Tg mouse model of early-onset AD. Imaging was performed on a 1 Tesla permanent magnet MR scanner using T1w-SE and FSE-IR sequences. ADx-001 was tested at three dose levels: 0.10, 0.15, and 0.20 mmol Gd/kg. Tg and age-matched WT control animals (n=6/dose level/genotype) were imaged pre-contrast and at 4 days after administration of ADx-001 (delayed post-contrast). Pre-contrast and delayed post-contrast images were qualitatively and quantitatively analyzed to determine sensitivity, specificity, and accuracy against post-mortem histological identification of amyloid-β plaque. The pharmacokinetics of ADx-001 were studied in monkeys and dogs. Blood samples were collected at multiple time points after administration of ADx-001, and Gd levels were analyzed by ICP-MS. The biodistribution of ADx-001 was studied in rats. Gd levels in target organs (liver, spleen, kidney, skin, bone, and brain) were determined by ICP-MS at day 4 and day 28 after administration of ADx-001.

Example 1: Preparation of ET3-73

Figure 4:
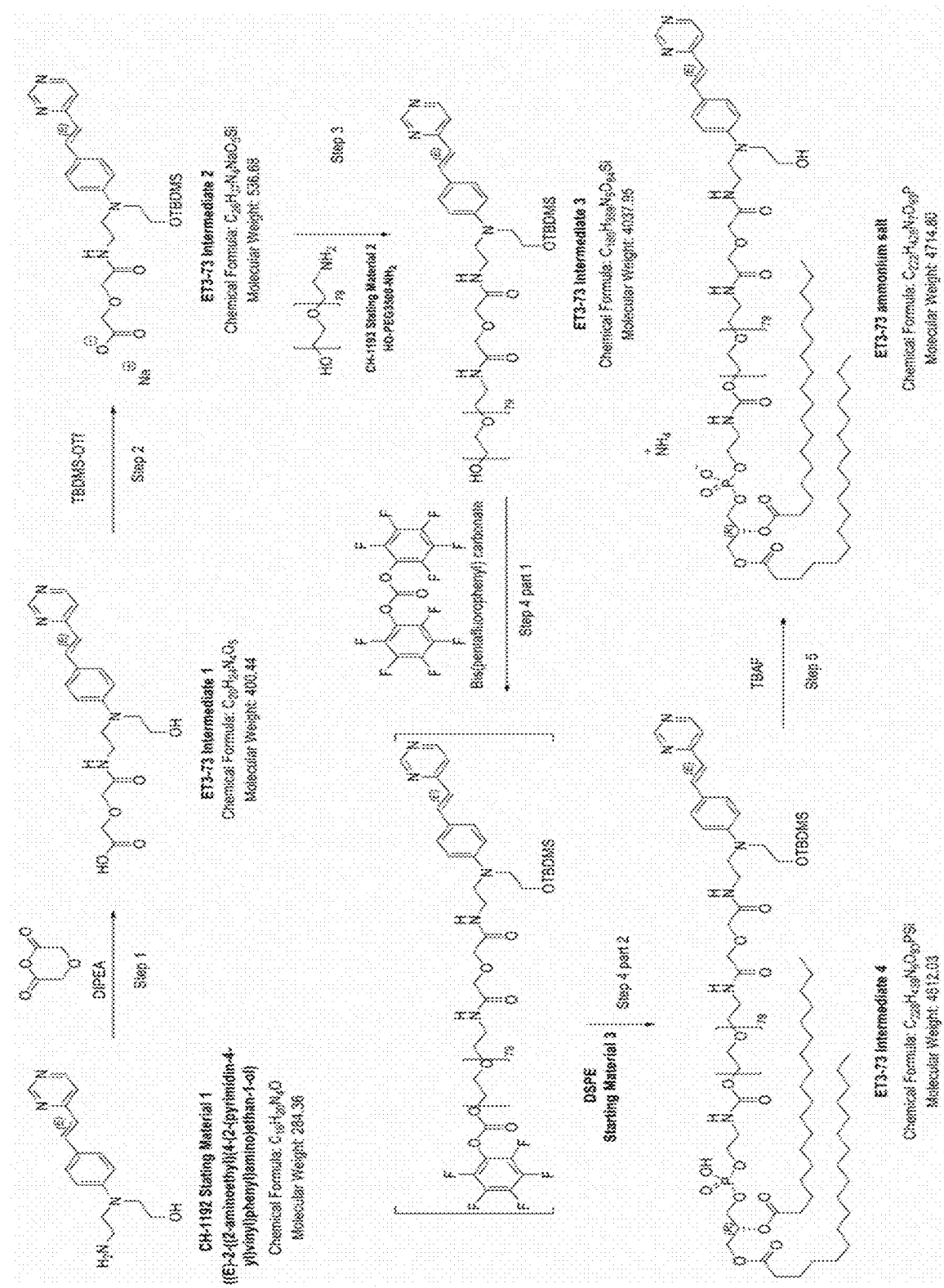
FIG. 4 provides an example synthetic scheme for the synthesis of ET3-73 ammonium salt.

With reference to FIG. 4, the starting material (E)-2-((2-aminoethyl)(4-(2-(pyrimidin-4-yl)vinyl)phenyl)amino)ethan-1-ol (SM1) was reacted with DIPEA to form ET3-73 Intermediate 1. ET3-73 Intermediate 1 was reacted with TBDMS-OTf (TBDMS-Triflate) to yield ET3-73 Intermediate 2. ET3-73 Intermediate 2 was coupled with HO-PEG3500-NH$_2$ (SM2) to form ET3-73 Intermediate 3. ET3-73 Intermediate 3 was reacted with bis-pentafluorophenyl-carbonate, and the activated ET3-73 Intermediate 3 was combined with DSPE that had been silylated using bis-trimethylsilyl-acetamide, to yield ET3-73 Intermediate 4. Finally, the ET3-73 ammonium salt was formed via deprotection using TBAF, followed by reaction with sodium ammonium acetate.

Example 2: Preparation of Gd(III)-DOTA-DSPE

Figure 5:
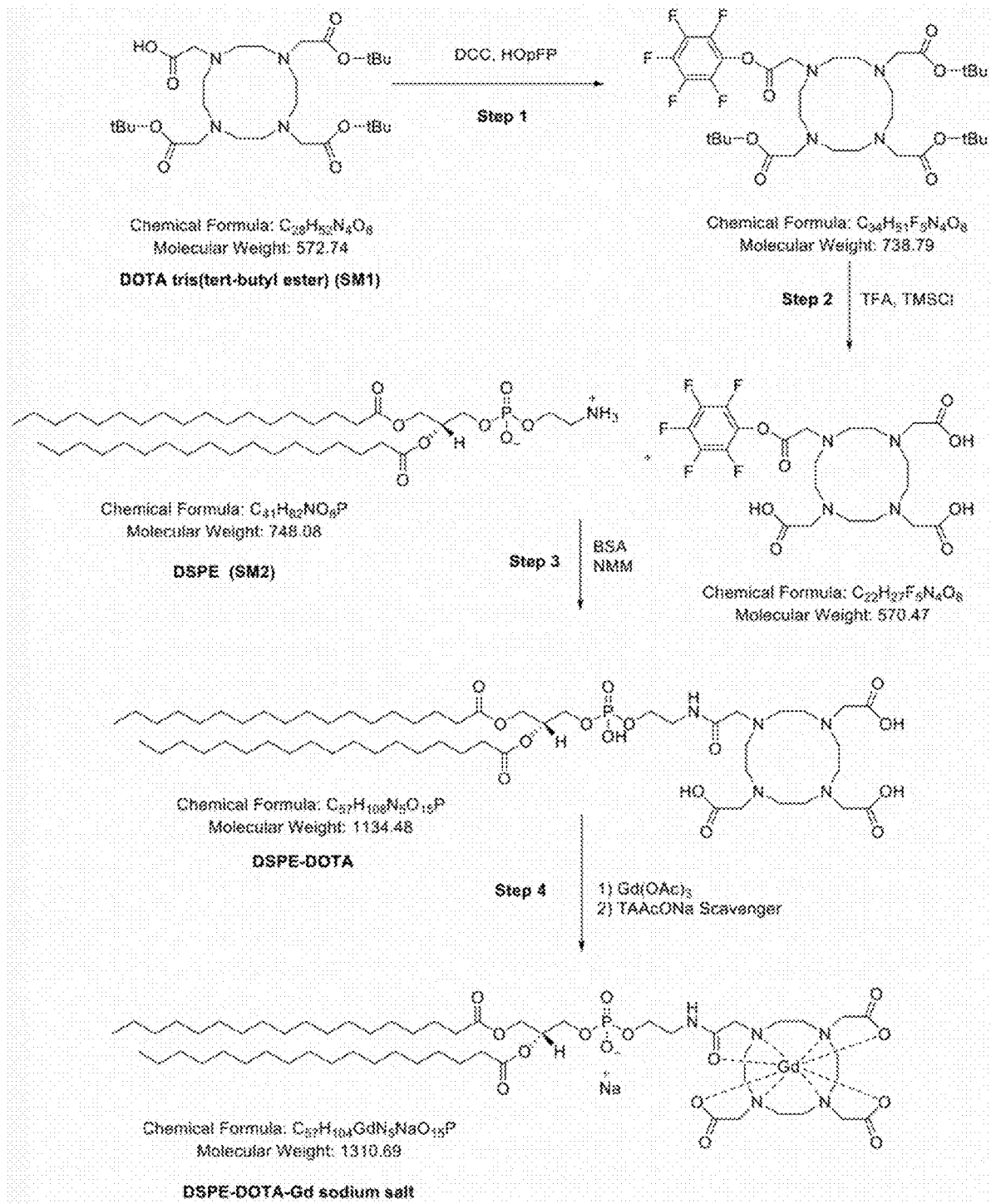
FIG. 5 provides an example synthetic scheme for the synthesis of Gd(III)-DOTA-DSPE sodium salt.

With reference to FIG. 5, the synthetic scheme starts with the further esterification of DOTA-tris(tert-butyl ester) (SM1) with pentafluorophenol (HOpFP). The tert-butyl ester protecting groups were removed using TFA and trimethylchlorsilane (TMSCl). The pentafluorophenyl ester was coupled to DSPE in the presence of BSA and NMM to form DSPE-DOTA. Chelation of gadolinium and salt formation occurred via addition of gadolinium as an acetate salt [Gd(OAc)3], followed by addition of the scavenger SiliaMetS TAAcONa (Triaminetetraacetate, sodium salt-functionalized silica gel) to form the final DSPE-DOTA-Gd sodium salt.

Example 3: Preparation of ADx-001

Figure 6:
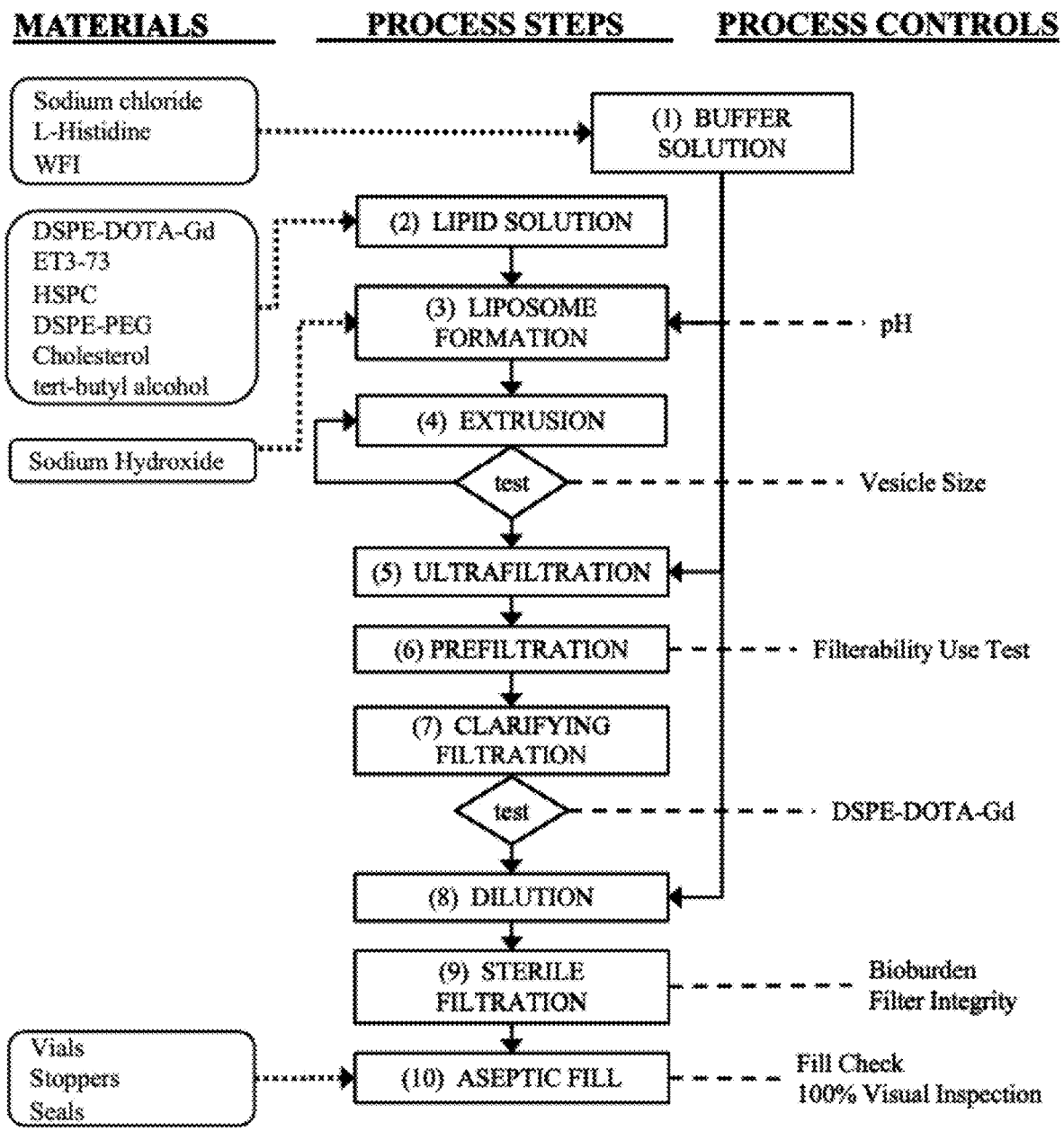
FIG. 6 shows an example process flow diagram for the preparation of ADx-001.

With reference to FIG. 6, ADx-001 was prepared as follows:

Step 1 (buffer solution): Sodium chloride and histidine were dissolved in water with mixing and filtered through a 0.2 µm filter. The solution was nominally pH 7.5.

Step 2 (lipid solution): DSPE-DOTA-Gd, HSPC (Lipoid Inc., Newark, N.J., USA), DSPE-mPEG$_{2000}$ (Corden Pharma, Liestahl, Switzerland), Chol (Lipoid Inc., Newark, N.J., USA), and ET3-73 (31.5:40:2.5:25:1 molar ratio) were dissolved in tert-butyl alcohol with mixing.

Step 3 (liposome formation): The lipid solution (step 2) was added to a portion of the buffer solution (step 1). The pH was adjusted to nominally pH 6.5-7.0 with sodium hydroxide solution, if necessary. This step generated liposomes of indeterminate size and lamellarity. The drug substance (DSPE-DOTA-Gd) and the other lipid components (HSPC, DSPE-mPEG$_{2000}$, Cholesterol, and ET3-73) reside within the lipid bilayer of the liposome.

Step 4 (extrusion): The process material was extruded through track-etch polycarbonate filters at elevated pressures in order to reduce the liposome vesicle size. Processing continued until the desired vesicle size (~140 nm nominal size) was achieved, as measured by an in-process dynamic light scattering test.

Step 5 (ultrafiltration): Ultrafiltration was performed on the process material using a tangential flow filtration assembly with a 500,000 molecular weight cut-off (MWCO) rating. During ultrafiltration, the liposome nanoparticles were re-circulated and retained by the ultrafilter, while a portion of the carrier solution (buffer solution plus solvent tert-butyl alcohol) passed through the ultrafilter into the permeate waste stream. The ultrafiltration step consisted of three sections. First, the process material was concentrated by discarding the permeate from the ultrafilter. Second, the ultrafiltration assembly was operated in a diafiltration mode, in which a constant concentration is maintained by replenishing the permeate waste stream with buffer solution (step 1). Third, the process material was concentrated in order to reach a slightly more concentrated level than the nominally 98 mg/mL total lipid composition of the final drug product.

Step 6 (prefiltration): The process material was passed through track-etch polycarbonate filters until the desired filterability was achieved.

Step 7 (clarifying filtration): The process material was passed through a 0.2 μm filter (Sartorius Sartopore® 2 XLI with polyethersulfone membrane).

Step 8 (dilution): The process material was diluted with buffer solution (Step 1) to the target label strength of 38.7 mg/mL DSPE-DOTA-Gd. The nominal concentration was 98 mg/L total lipid.

Step 9 (sterile filtration): Under aseptic conditions, the process material was passed through a 0.2 μm sterilizing-grade filter (Sartorius Sartopore® 2 XLI with polyethersulfone membrane).

Step 10 (aseptic fill): Under aseptic conditions, the process material was filled into vials, stoppered, and sealed. Fill weight checks were performed during the filling operation, and filled vials were 100% visually inspected for particulates and container-closure defects. Batch data for multiple example batches is set forth in Table 1:

0.10, 0.15, and 0.20. At each dose level, ADx-001 was tested in Tg (n=6) and WT (mice that lacked both mutations) mice (n=6). ADx-001 was intravenously administered as a slow bolus injection via tail vein.

Imaging was performed on a 1T permanent MRI scanner (M7 system, Aspect Imaging, Shoham, Israel). Animals were sedated using 2.5 or 3% isoflurane and placed on a custom fabricated sled with an integrated face-cone for continuous anesthesia delivery by inhalation (1-2% isoflurane). Respiration rate was monitored by a pneumatically controlled pressure pad placed underneath the abdominal region. Two MRI sequences were tested: a T1w-SE sequence and a 2D FSE-IR that approximates a fluid-attenuated inversion recovery sequence. SE parameters were: TR=600 ms, TE=11.5 ms, slice thickness=1.2 mm, matrix=192×192, FOV=30 mm, slices=16, NEX=4. FSE-IR parameters were: TR=6500 ms, TE=80 ms, TI=2000 ms, slice thickness=2.4 mm, matrix=192×192, FOV=30 mm, slices=6, NEX=6. Coil calibrations, RF calibration, and shimming were performed at the beginning of the study for each subject. All animals underwent pre-contrast scans followed by intravenous administration of ADx-001. Delayed post-contrast scans were acquired four days after administration of contrast agent. Pre-contrast and post-contrast scans were acquired using both T1w-SE and FSE-IR sequences.

Animals were euthanized after post-contrast scans and perfused with 0.9% saline followed by 4% formalin solution. The brains were excised, fixed in 4% formalin solution for 24 hours, and transferred to 30% sucrose for cryopro-

TABLE 1

| | Batch Data | | | |
|---|---|---|---|---|
| Attribute | 1 | 2 | 3 | 4 |
| Visual Appearance | Yellow to off-yellow translucent liquid, free of visible particulates | Yellow to off-yellow translucent liquid, free of visible particulates | Yellow to off-yellow translucent liquid, free of visible particulates | Yellow to off-yellow translucent liquid, free of visible particulates |
| pH | 7.7 | 7.5 | 7.3 | 7.3 |
| Osmolality | 274 mOsmol/kg | 277 mOsmol/kg | 295 mOsmol/kg | 311 mOsmol/kg |
| Vesicle Size (Dynamic Light Scattering) | Z-avg: 140 nm<br>D10: 86 nm<br>D50: 155 nm<br>D90: 268 nm<br>PDI: 0.2 | Z-avg: 98 nm<br>$D_{10}$: 63 nm<br>$D_{50}$: 106 nm<br>$D_{90}$: 178 nm<br>PDI: 0.1 | Z-avg: 103 nm<br>$D_{10}$: 66 nm<br>$D_{50}$: 111 nm<br>$D_{90}$: 189 nm<br>PDI: 0.1 | Z-avg: 115 nm<br>$D_{10}$: 78 nm<br>$D_{50}$: 122 nm<br>$D_{90}$: 192 nm<br>PDI: 0.1 |
| DSPE-DOTA-Gd Content | 30.78 mg/mL | 41.32 mg/mL | 38.85 mg/mL | 33.73 mg/mL |
| ET3-73 Content | 2.22 mg/mL | 2.82 mg/mL | 2.88 mg/mL | 2.29 mg/mL |
| HSPC Content | 23.57 mg/mL | 31.49 mg/mL | 30.49 mg/mL | 28.37 mg/mL |
| DSPE-PEG Content | 5.62 mg/mL | 6.67 mg/mL | 6.78 mg/mL | 6.32 mg/mL |
| Cholesterol Content | 14.47 mg/mL | 18.37 mg/mL | 18.55 mg/mL | 17.07 mg/mL |
| Stearic Acid | <400 μg/mL | <200 μg/mL | <200 μg/mL | <200 μg/mL |
| Residual Solvents | 13 ppm | 12 ppm | 16 ppm | 54 ppm |
| Free Gd | <2.5 μg/mL | <2.5 μg/mL | <2.5 μg/mL | <2.5 μg/mL |

Example 4: MRI Study

Studies were performed in an APPswe/PSEN1dE9 (C57BL/6J background, 11-18 months age) double Tg mouse model of early-onset AD (JAX MMRRC Stock #005864). The Tg mice develop amyloid plaques in the brain around 6-7 months of age. ADx-001, as prepared in Example 3, was tested at three dose levels (mmol Gd/kg):

tection. Brains were embedded in OCT and stored at −80° C. until ready for sectioning. 15 μm thick brain sections were cut and used for post-mortem phenotypic confirmation of amyloid deposition. Sections were incubated in 5% Bovine Serum Albumin ("BSA") for 1 hour, followed by incubation with fluorescent-tagged anti-amyloid β antibody (AF647-4G8, BioLegend, San Diego, Calif.) in 3% BSA at 4° C. overnight. Sections were further stained with a nuclear marker (DAPI), washed, mounted, cover-slipped using Vectashield mounting medium (Vector Laboratories, Burlingame Calif.), and imaged on a confocal microscope with appropriate filter sets. The presence of amyloid bound ADx-001 nanoparticles was analyzed by imaging in FITC channel.

Figure 7:
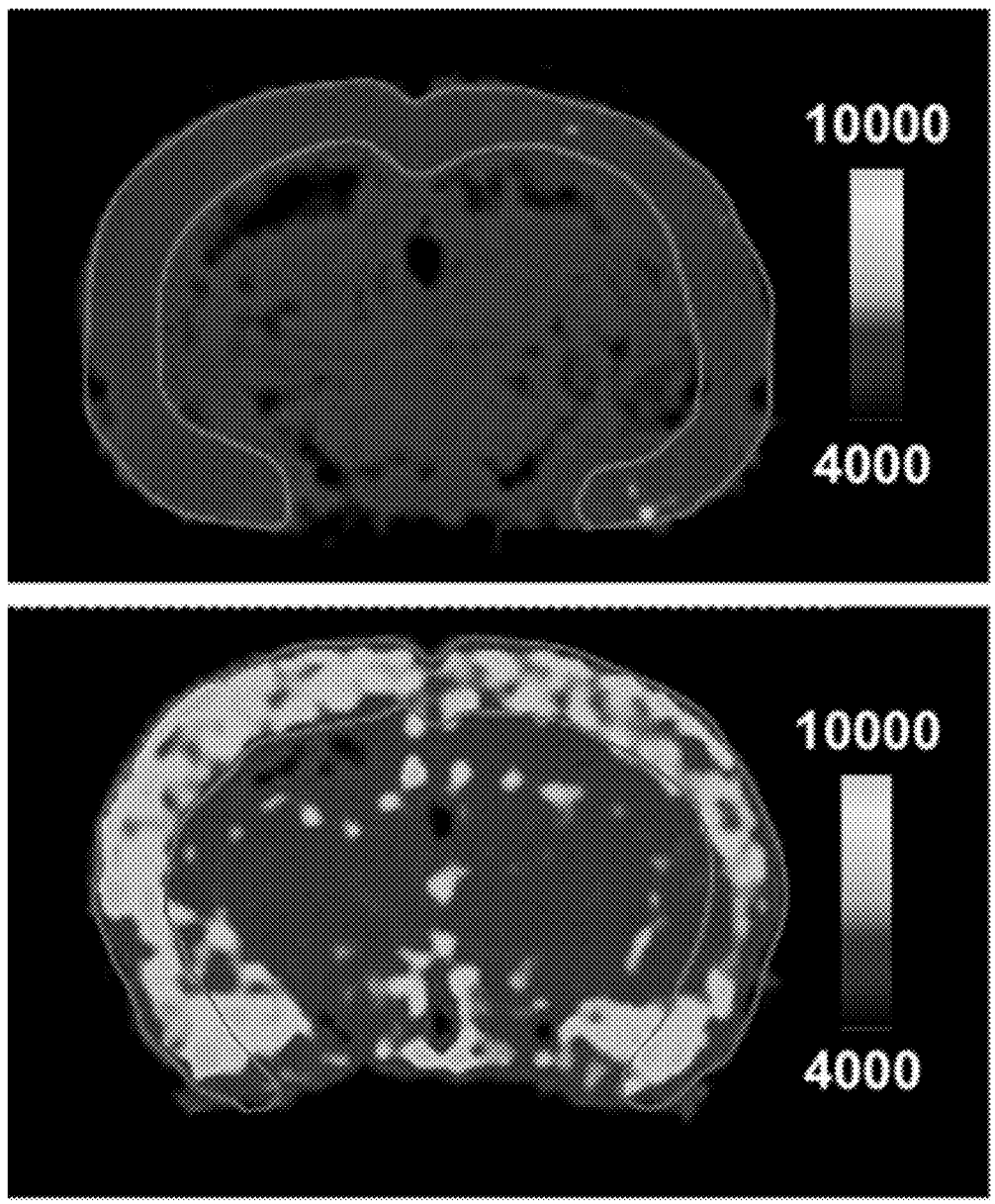
FIG. 7 shows a demonstration of cortical regions of interest (ROIs) identification in axial MR images of the brain. Cortical ROIs are outlined on FSE-IR brain images pre- (upper) and post- (lower) contrast.

Qualitative and quantitative analyses of MRI images were performed in OsiriX (version 5.8.5, 64-bit) and MATLAB (version 2015a). Brain extraction was performed through a combination of threshold and manual segmentation in OsiriX. Signal change between pre-contrast and delayed post-contrast images was assessed through quantification of signal intensity in cortical regions near the center of the image stack (see FIG. 7). Amyloid-positive animals were identified through qualitative assessment of signal enhancement between pre-contrast and delayed post-contrast assessment of the cortex and hippocampus. The change in signal between pre-contrast and post-contrast images was quantified through integration of signal in ROIs that encompassed cortical tissue in central slices of the MRI volume. Signal change (%) was calculated as in Eq. 1:

$$\text{Signal change}(\%) = 100 \times \frac{SI_{Past} - SI_{Pre}}{SI_{PRe}} \quad \text{Eq. 1}$$

An observation of signal enhancement in MRI of an amyloid-positive animal (as determined by immunofluorescence) was counted as a true positive result. Conversely, the absence of signal enhancement between pre-contrast and delayed post-contrast images for an amyloid-negative animal was considered a true negative. Sensitivity was determined by the ratio of MRI-identified true positives to the total number of true positives identified by the gold standard of post-mortem amyloid plaque staining through immunofluorescence analysis. Specificity was determined as the ratio of MRI-identified true negatives to the total number of true negatives. Overall accuracy was calculated as the total number of animals correctly identified by MRI compared with post-mortem immunofluorescence-determined amyloid true positives.

Figure 8:
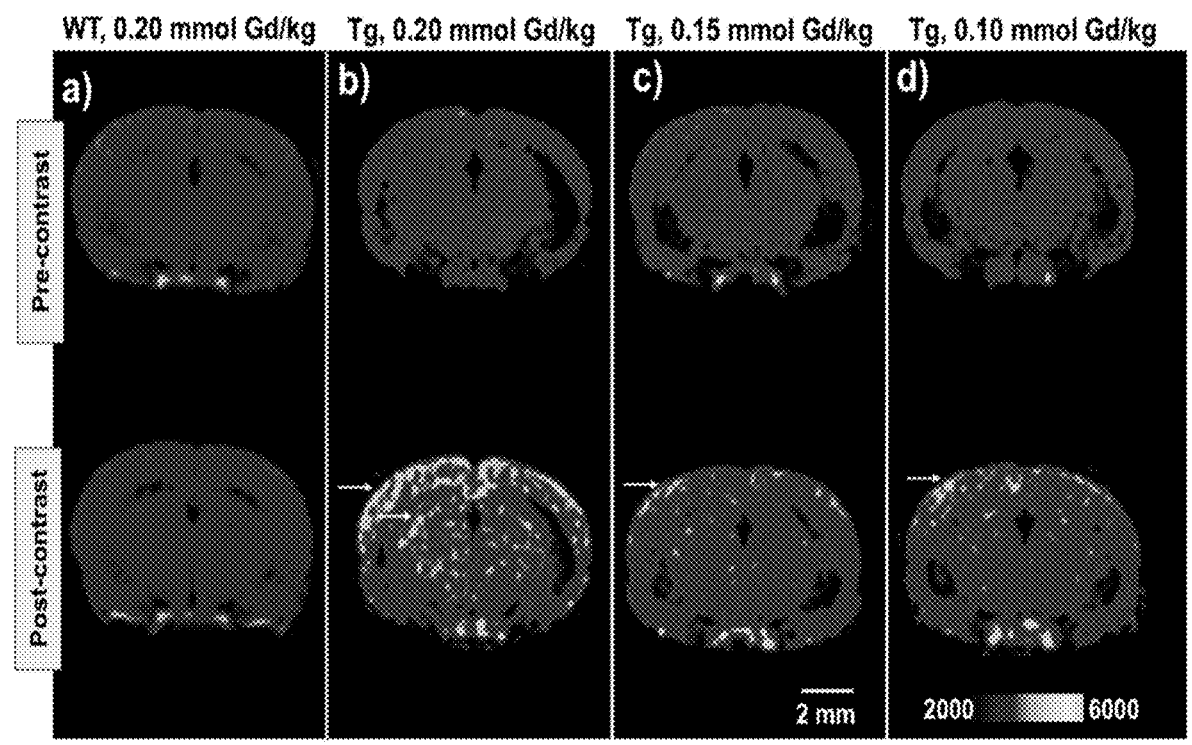
FIG. 8 shows pre- and post-ADx-001 administration T1-weighted spin-echo ("T1w-SE") axial images of the brain: a) of a wild-type ("WT") mouse (amyloid-negative) at a dose of 0.20 mmol Gd/kg; and of Tg APPswe/PSEN1dE9 ("Tg") mice (amyloid-positive) at doses of: b) 0.20 mmol Gd/kg; c) 0.15 mmol Gd/kg; and d) 0.10 mmol Gd/kg. Arrows point to regions of signal enhancement in the cortex and hippocampus.

WT mice (amyloid-negative) did not demonstrate brain signal enhancement in delayed post-contrast images acquired using T1w-SE or FSE-IR at any dose level of ADx-001. However, Tg mice (amyloid-positive) demonstrated moderate to high MR signal enhancement in the cortical and hippocampal regions in T1w-SE delayed post-contrast images at ADx-001 dose of 0.20 and 0.15 mmol Gd/kg. Thus, as shown in FIG. 8: a) a WT animal administered 0.2 mmol Gd/kg of ADx-001 shows no signal enhancement four days after injection; b) a Tg animal shows high enhancement in cortical (upper arrow) and hippocampal regions (lower arrow) four days after administration of 0.2 mmol Gd/kg of ADx-001; c) a Tg animal shows moderate enhancement in cortical (upper arrow) and hippocampal (lower arrow) regions four days after administration of 0.15 mmol Gd/kg of ADx-001; and d) a Tg animal shows low enhancement in cortical region (arrow) four days after administration of 0.10 mmol Gd/kg of ADx-001.

Figure 9:
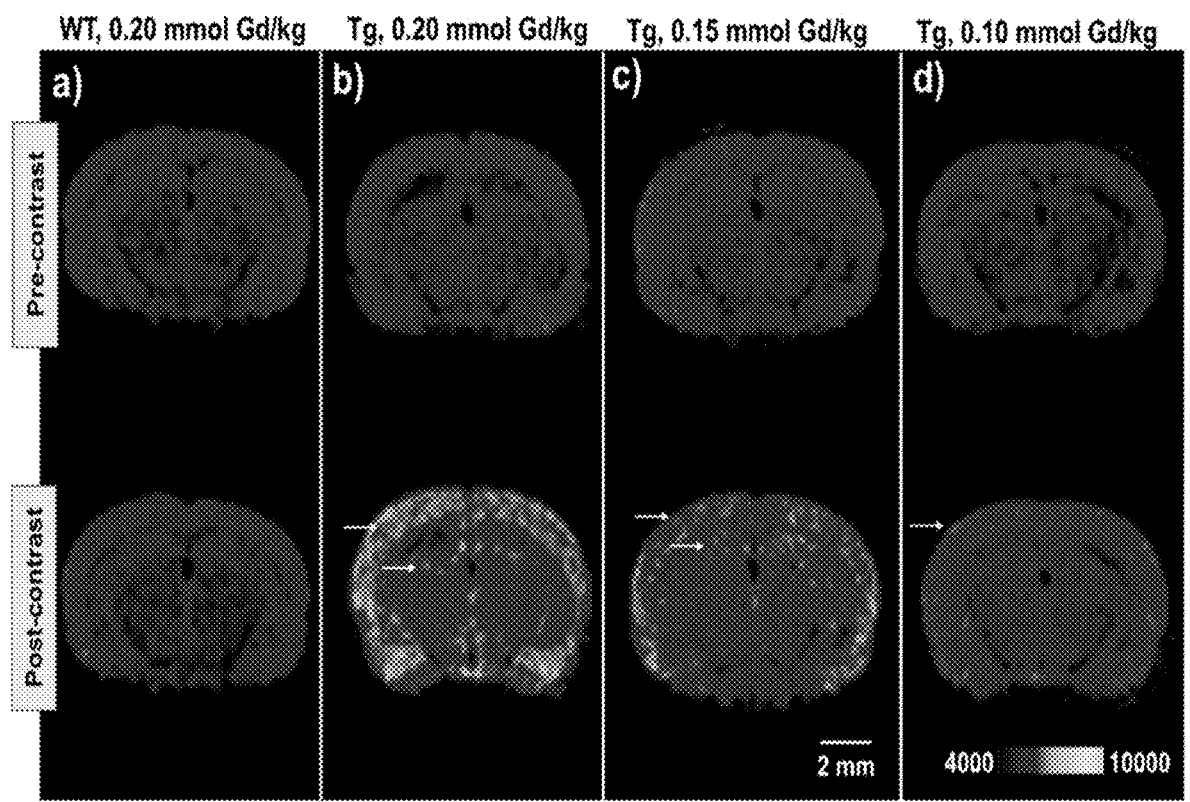
FIG. 9 shows pre- and post-ADx-001 administration fast spin-echo inversion recovery ("FSE-IR") axial images of the brain: a) of a WT mouse at a dose of 0.20 mmol Gd/kg; and of Tg mice at doses of: b) 0.20 mmol Gd/kg; c) 0.15 mmol Gd/kg; and d) 0.10 mmol Gd/kg. Arrows point to regions of signal enhancement in the cortex and hippocampus.

Similarly, Tg mice demonstrated moderate to high signal enhancement in delayed post-contrast FSE-IR images at an ADx-001 dose of 0.20 and 0.15 mmol Gd/kg, and relatively mild signal enhancement at 0.10 mmol Gd/kg. As shown in FIG. 9, FSE-IR axial images demonstrate MR signal enhancement in ADx-001 delayed post-contrast scans of Tg APPswe/PSEN1dE9 mice but not in age-matched, WT control mice. Specifically: (a) a WT animal administered 0.20 mmol Gd/kg ADx-001 demonstrates no signal enhancement in delayed post-contrast images; (b) a Tg animal administered 0.20 mmol Gd/kg ADx-001 shows high signal enhancement in the cortical (upper arrow) and hippocampal (lower arrow) regions in delayed post-contrast images; (c) a Tg animal administered 0.15 mmol Gd/kg ADx-001 shows moderate signal enhancement in cortical region (upper arrow) and low enhancement in hippocampal region (lower arrow) in delayed post-contrast images; and (d) a Tg animal administered 0.10 mmol Gd/kg ADx-001 shows low signal enhancement in cortical region (arrow) in delayed post-contrast images. All delayed post-contrast images were acquired four days after administration of ADx-001.

Figure 10:
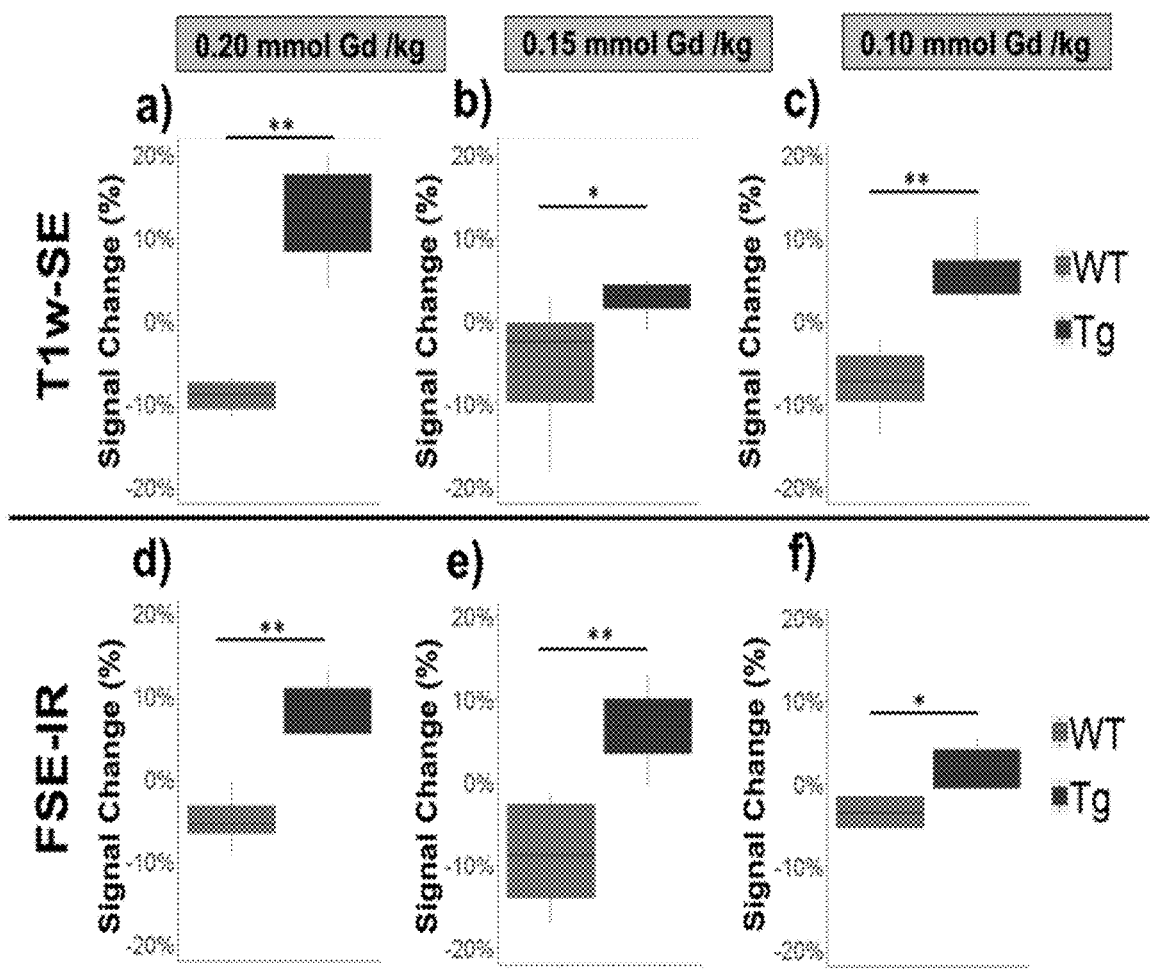
FIG. 10 demonstrates that Tg mice exhibit MR signal enhancement in cortical brain regions relative to WT counterparts at all dose levels of ADx-001. The box plots show statistically significant differences in signal changes (expressed as percentage) between pre-contrast and delayed post-contrast T1w-SE images for: a) 0.20 mmol Gd/kg; b) 0.15 mmol Gd/kg; and c) 0.10 mmol Gd/kg dose levels of ADx-001, and between pre-contrast and delayed post-contrast FSE-IR images for: d) 0.20 mmol Gd/kg; e) 0.15 mmol Gd/kg; and f) 0.10 mmol Gd/kg dose levels.

Quantitative analysis of cortical ROIs confirmed qualitative observations of MR signal enhancement in post-contrast delayed images and found a statistically significant difference in post-contrast signal change between Tg and WT animals at all dose levels. As shown in FIG. 10, Tg mice demonstrate MR signal enhancement in cortical brain regions relative to WT counterparts at all dose levels of ADx-001. Specifically, box plots show signal changes (expressed as percentage) between pre-contrast and delayed post-contrast T1w-SE images for: a) 0.20 mmol Gd/kg; b) 0.15 mmol Gd/kg; and c) 0.10 mmol Gd/kg dose levels of ADx-001. Similar signal changes are shown between pre-contrast and delayed post-contrast FSE-IR images for: d) 0.20 mmol Gd/kg; e) 0.15 mmol Gd/kg; and f) 0.10 mmol Gd/kg dose levels. A Wilcoxon rank-sum statistical test was applied to compare group differences. Values of $p \leq 0.05$ were considered statistically significant. In FIG. 10, $p < 0.05$ (*) and $p < 0.005$ (**).

Figure 11:
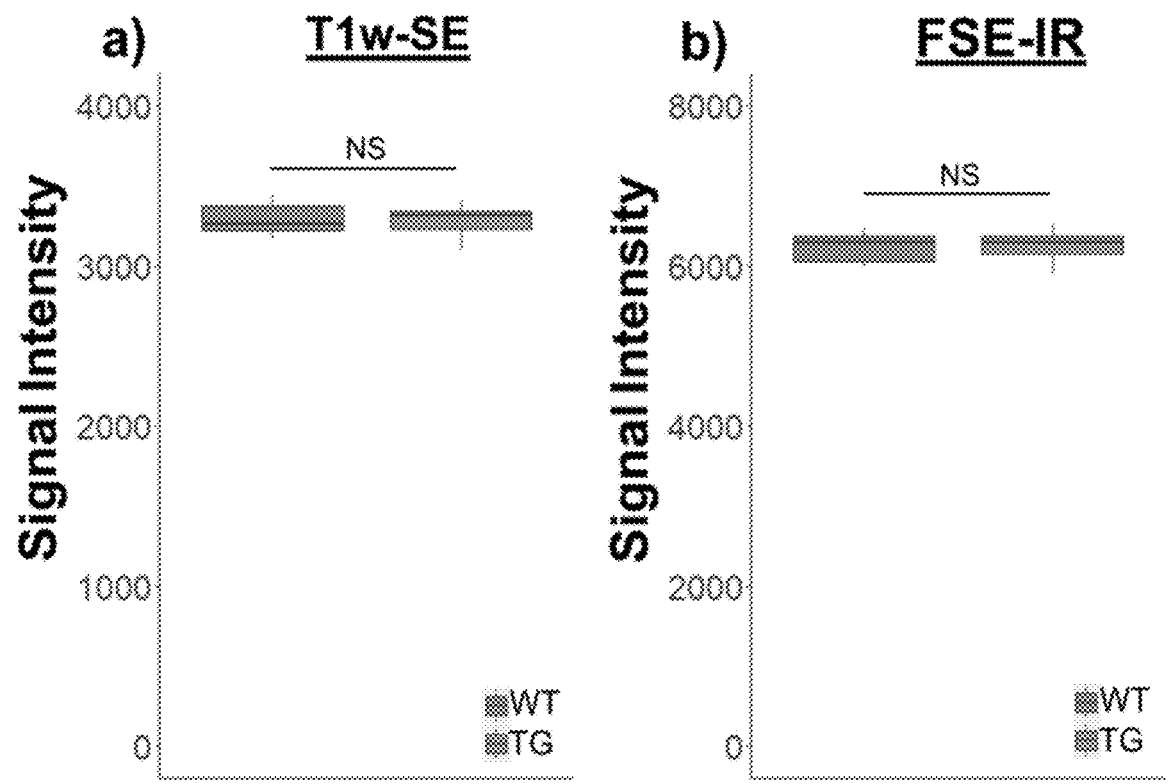
FIG. 11 shows the signal intensity mean and range for (a) T1w-SE and (b) FSE-IR sequences for pre-contrast scans of both WT (n=18) and Tg (n=18) mice. ROIs were drawn in the cortex for each animal. No significant differences (NS) were found between signal intensities for WT and Tg mice for either T1w-SE or FSE-IR sequences.

A signal variance threshold was estimated from pre-contrast (baseline) scans of all tested mice after establishing that the pre-contrast signal for WT and Tg mice was indistinguishable (see FIG. 11). Estimated baseline signal thresholds were: 5.1% (FSE-IR) and 5.6% (T1w-SE). Amyloid-positive mice were identified if they demonstrated signal enhancement above these cutoffs.

Using these thresholds, ADx-001 demonstrated excellent specificity (100%) at all dose levels using both T1w-SE and FSE-IR sequences. As shown in Table 2, below, in T1w-SE imaging, ADx-001 demonstrated high sensitivity (>80%) at 0.20 and 0.10 mmol Gd/kg dose levels, whereas in FSE-IR imaging, ADx-001 demonstrated high sensitivity (>80%) at the 0.20 and 0.15 mmol Gd/kg dose levels. In both T1w-SE and FSE-IR, ADx-001 demonstrated the highest accuracy (>90%) at the highest dose level (0.20 mmol Gd/kg).

TABLE 2

| ADx-001 Dose (mmol Gd/kg) | T1w-SE | | | FSE-IR | | |
|---|---|---|---|---|---|---|
| | Accuracy | Sensitivity | Specificity | Accuracy | Sensitivity | Specificity |
| 0.20 | 100% | 100% | 100% | 91.7% | 83.3% | 100% |
| 0.15 | 83.3% | 66.7% | 100% | 91.7% | 83.3% | 100% |
| 0.10 | 91.7% | 83.3% | 100% | 75% | 50% | 100% |

Figure 12:
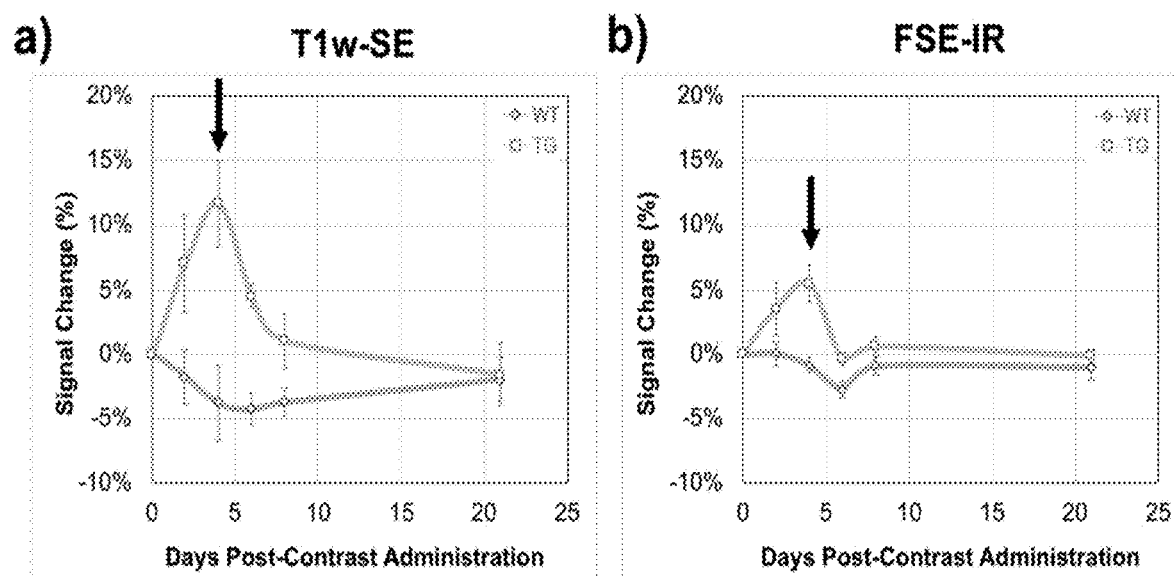
FIG. 12 shows the cortical brain signal change as a function of time in WT (n=3) and Tg (n=3) mice in a) T1w-SE and b) FSE-IR sequences. Maximum signal enhancement was seen at day 4 post-contrast (arrow). Tg animals demonstrated signal enhancement relative to WT animals in both sequences. The signal returned to near baseline levels by day 21.

Longitudinal imaging studies in WT and Tg mice demonstrated that signal enhancement was optimal four days post-contrast administration, and that signal had returned to near baseline levels by 21 days post-contrast administration (see FIG. 12).

Figure 13:
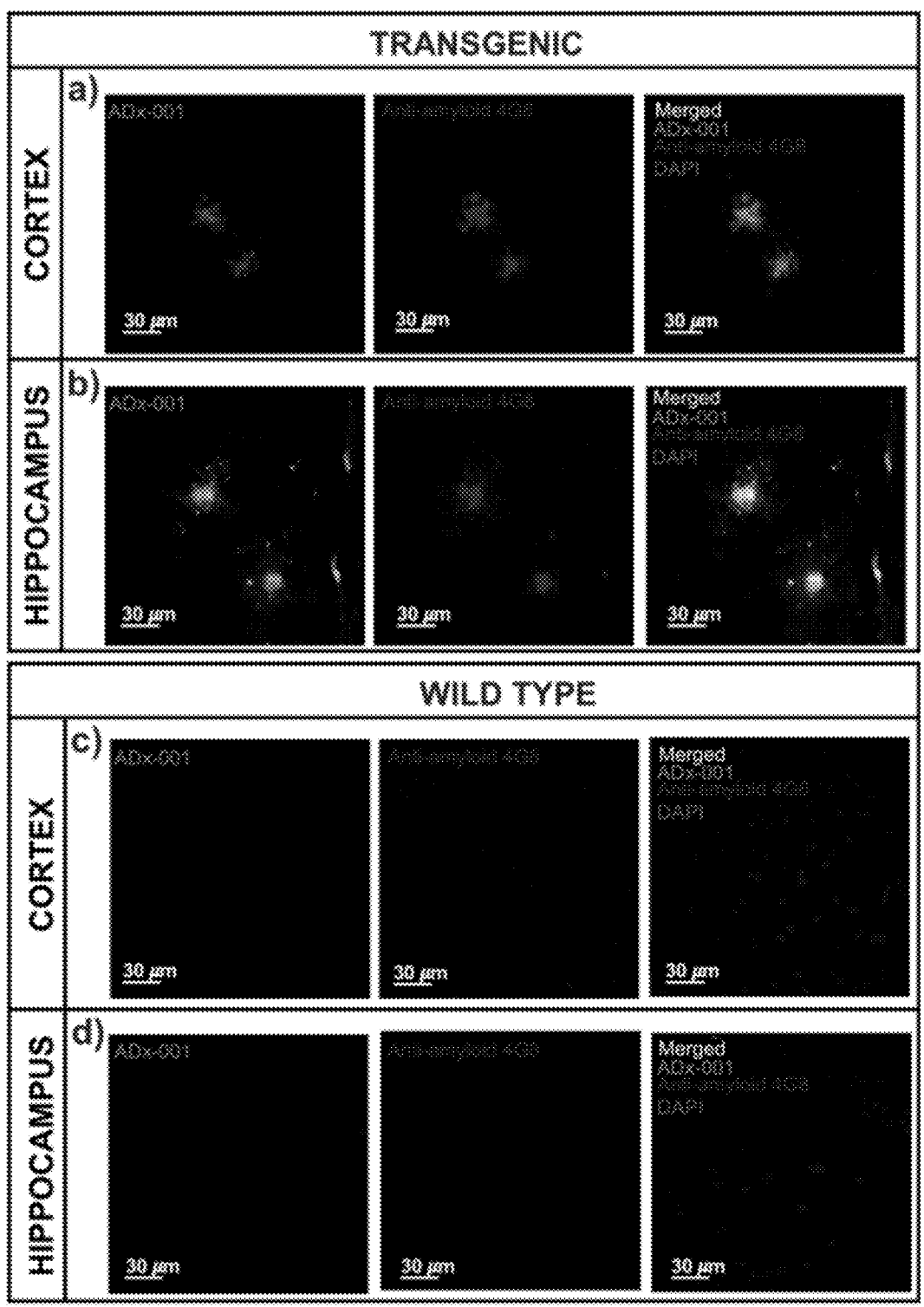
FIG. 13 provides post-mortem confirmation of ADx-001 binding to β-amyloid plaques via representative fluorescence microscopy images of ADx-001 binding to amyloid plaques in a) mouse cortex and b) hippocampus regions in a Tg animal, as compared to representative images for c) WT cortex and d) hippocampus regions in a WT animal.

Immunofluorescence microscopy analysis confirmed preferential concentration and co-localization of ADx-001 with amyloid plaque deposits in cortex and hippocampus regions in Tg mice. In comparison, WT animals did not demonstrate amyloid plaque deposits or show the presence of bound ADx-001 nanoparticles. FIG. 13 shows representative fluorescence microscopy images of ADx-001 binding to amyloid plaques in mouse cortex a) and hippocampus b) regions in a Tg animals. Representative images are also shown for WT cortex c) and hippocampus d) regions. WT mice did not show evidence of amyloid plaque deposits (4G8 antibody staining) or presence of bound ADx-001 (observing for amyloid ligand fluorescence signal). Images were acquired at 60× magnification.

Example 5: Pharmacokinetic Studies

The pharmacokinetics ("PK") of ADx-001 were evaluated in cynomolgus monkeys and beagle dogs. Non-naïve male cynomolgus monkeys (n=3, 2-5 yr age, 2.3-3.1 kg body weight) were intravenously administered ADx-001 using a calibrated infusion pump over ~60 min at 0.30 mmol Gd/kg. Blood samples were collected from all animals at pre-dose, immediately post-end of infusion, and 4, 8, 24, 48, 96, 168, 336, and 672 hours post-start of injection ("SOI"). For PK analysis in beagle dogs, animals (n=5, 5-7 months age, 6.2-7.9 kg body weight) were intravenously infused ADx-001 over ~60 min at 0.30 mmol Gd/kg. Blood samples were processed to plasma and stored frozen until ready for analysis.

Gd concentration in plasma samples was determined using ICP-MS. Plasma samples (100 µL) were digested in 90% concentrated $HNO_3$ (750 µL) at 90° C. for 15 min. The digested samples were diluted in deionized ("DI") water, centrifuged at 3000 rpm for 15 min, and the supernatant was further diluted for ICP-MS analysis such that the Gd concentrations fell within the range of ICP-MS calibration standards (1-500 ppb).

Figure 14:
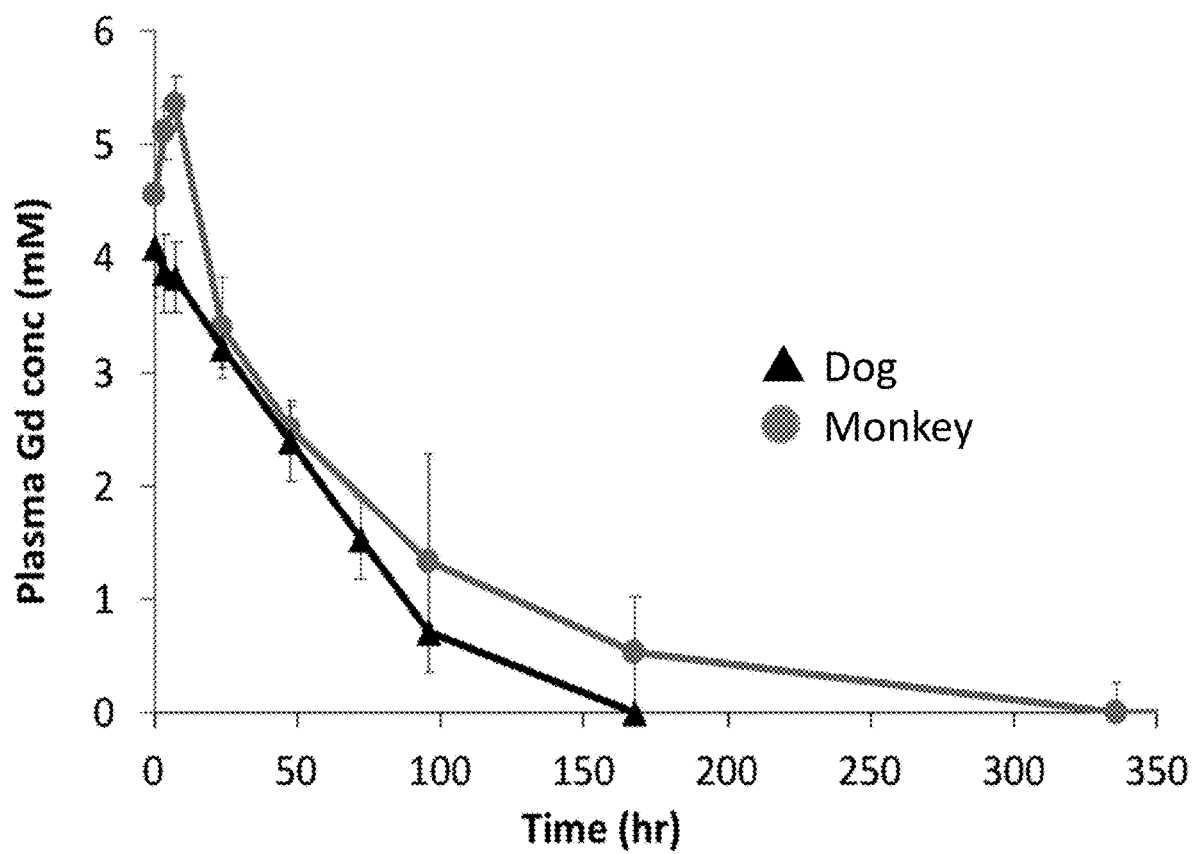
FIG. 14 shows plasma Gd concentrations determined using inductively-coupled plasma mass spectrometry ("ICP-MS") at various time points after administration of ADx-001 in dogs (▲) and monkeys (●).

ADx-001 was well tolerated in dogs and monkeys with no adverse effects. FIG. 14 demonstrates a long blood half-life for ADx-001. Plasma Gd concentrations were determined using ICP-MS at various time points after administration of ADx-001 to the dogs (▲) and monkeys (●). Assuming first-order kinetics, the elimination rate was 0.017 $hour^{-1}$, resulting in a blood half-life of approximately 41 hours in monkeys. Plasma levels of Gd declined by 80% at 96 hours post-SOI and by greater than 99% at 336 hours post-SOI in monkeys. While there is a lack of literature on blood half-life of comparable liposome-based MRI contrast agents in monkeys, studies in mice have shown a blood half-life in the 14-24 hr range. In dogs, the elimination rate was 0.0297 $hr^{-1}$, resulting in a blood half-life of approximately 23 hours. Plasma levels of Gd declined by ~85% at 96 hours post-SOI and ~99% at 168 hr post-SOI in dogs.

Example 6: Tissue Biodistribution

The biodistribution of ADx-001 was studied in a rat model. Wistar Han rats (10 weeks age, 257-296 g body weight; n=13 per treatment group) were administered ADx-001 at 0.15 mmol Gd/kg (n=13) or 0.30 mmol Gd/kg as a single intravenous bolus injection. Animals were euthanized at Day 4 (n=7/dose level) and Day 28 (n=6/dose level) post-administration of ADx-001. Tissues were harvested to determine Gd levels in target organs (liver, spleen, kidney, skin, bone, and brain). Tissue samples were frozen immediately in liquid nitrogen and stored at −20° C. until ready for analysis.

Gd concentration in tissue samples was quantified using ICP-MS. Wet tissue (~100 mg) was digested in 90% concentrated $HNO_3$ (~750 µL) at 90° C. for 10-15 min. The digested sample was diluted in DI water, vortexed vigorously, and centrifuged at 3500 rpm for 15 min. The supernatant was separated and further diluted as needed to ensure Gd concentrations fell within the range of calibration standards (1-500 ppb). Quality control samples (50 and 100 ppb) were included at the start, middle, and end of analysis runs.

Figure 15:
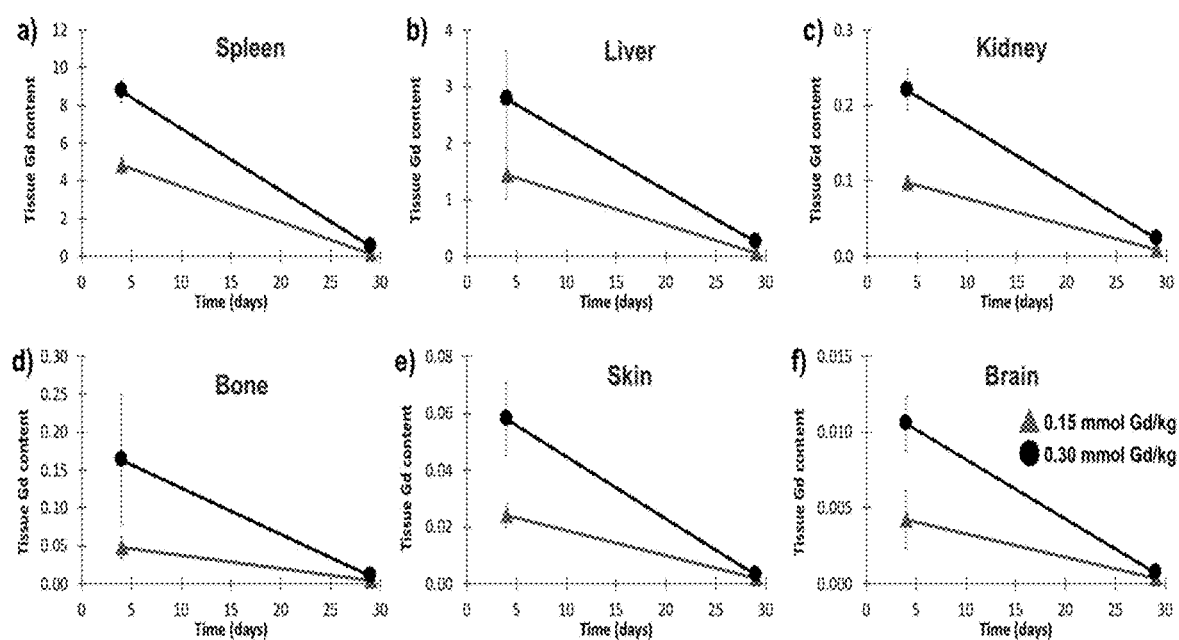
FIG. 15 shows the biodistribution of ADx-001 in a rat a) spleen, b) liver, c) kidney, d) bone, e) skin, and f) brain at day 4 and day 28 after intravenous administration of ADx-001 at 0.15 mmol Gd/kg dose level (▲) and 0.3 mmol Gd/kg dose level (●), as determined by ICP-MS analysis.

ADx-001 was well tolerated in rats at doses up to 0.30 mmol Gd/kg, with no observable adverse effects on clinical toxicity, clinical pathology, or histopathology endpoints (data not shown). Tissue Gd levels showed a dose-related increase in all organs. Thus, FIG. 15 shows ICP-MS analyses illustrating the Gd levels in a) spleen; b) liver; c) kidney; d) bone; e) skin; and f) brain at day 4 and day 28 after intravenous administration of ADx-001 at 0.15 mmol Gd/kg dose level (▲) and 0.3 mmol Gd/kg dose level (●). Tissue Gd content is expressed as mg Gd per gram of wet tissue. The highest Gd tissue levels were observed in liver and spleen, consistent with known organs for clearance of PEGylated liposomal agents. The lowest Gd levels were observed in the brain. Tissue levels of Gd at day 28 were reduced by more than 90% compared to Gd tissue levels at day 4 in all organs.

Animal studies were performed under a protocol approved by the Institutional Animal Care and Use Committee. The studies were in compliance with NC3RS-ARRIVE guidelines.

ADx-001-enhanced MRI demonstrated significantly higher ($p<0.05$) brain signal enhancement in Tg mice (amyloid-positive) relative to WT (amyloid-negative) mice at all dose levels. ADx-001-enhanced T1w-SE imaging demonstrated high sensitivity (>80%) at 0.10 and 0.20 mmol Gd/kg, whereas ADx-001-enhanced FSE-IR imaging demonstrated high sensitivity (>80%) at 0.15 and 0.20 mmol Gd/kg. Excellent specificity (100%) was observed at all dose levels of ADx-001. Pharmacokinetic studies demonstrated long blood half-life (23 hours in dogs and 41 hours in monkeys). Biodistribution studies demonstrated systemic clearance of ADx-001 primarily via the mononuclear phagocytic system (also known as the reticuloendothelial system). Tissue Gd levels in all organs at day 28 were reduced by greater than 90% compared to day 4, suggesting on-going clearance.

In short, the amyloid-targeted liposomal macrocyclic gadolinium contrast agent, ADx-001, demonstrated high sensitivity and excellent specificity for in vivo imaging of β-amyloid plaques in mouse brain. No signs of toxicity were detected, and the pharmacokinetics followed expected patterns for PEGylated nanoparticles.

Unless otherwise specified, "a," "an," "the," "one or more of," and "at least one" are used interchangeably. The singular forms "a", "an," and "the" are inclusive of their plural forms. The recitations of numerical ranges by endpoints include all numbers subsumed within that range (e.g., 1 to 5 includes 1, 1.5, 2, 2.75, 3, 3.80, 4, 5, etc.). The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

The invention claimed is:
1. A liposomal composition, comprising:
a first phospholipid;
a sterically bulky excipient that is capable of stabilizing the liposomal composition;
a second phospholipid that is derivatized with a first polymer;
a macrocyclic gadolinium-based imaging agent; and
a third phospholipid that is derivatized with a second polymer, the second polymer being conjugated to a targeting ligand, the targeting ligand being represented by:

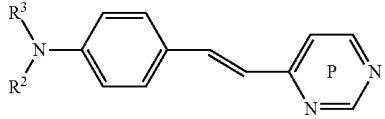

wherein,
Pyrimidine "P" may be substituted with zero, one, or more of —OH, O-alkyl, and —NH$_2$;
R$^2$ is a linking group comprising C$_1$-C$_6$ alkyl or C$_1$-C$_6$ alkoxyalkyl; and
R$^3$ is hydrogen, C$_1$-C$_6$ alkyl, or C$_1$-C$_6$ alkoxyalkyl, and R$^3$ other than hydrogen is substituted with zero, one, or more —OH, and
wherein the third phospholipid that is derivatized with a second polymer comprises:

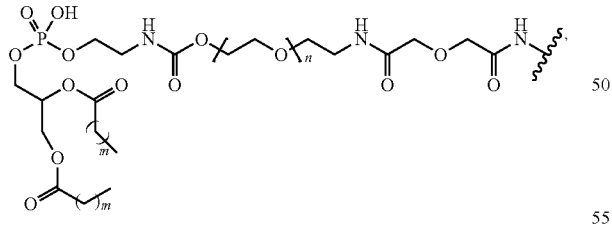

or a salt thereof, wherein the variable n is any integer from about 70 to about 90, and wherein the variable m is one of: 12, 13, 14, 15, 16, 17, or 18.

2. The liposomal composition of claim 1, wherein the first phospholipid comprises hydrogenated soy L-α-phosphatidylcholine ("HSPC").

3. The liposomal composition of claim 1, wherein the sterically bulky excipient that is capable of stabilizing the liposomal composition comprises cholesterol ("Chol").

4. The liposomal composition of claim 1, wherein the second phospholipid that is derivatized with a first polymer comprises 1,2-distearoyl-sn-glycero-3-phosphoethanolamine-N-(methoxy (polyethylene glycol)-2000) ("DSPE-mPEG2000").

5. The liposomal composition of claim 1, wherein the macrocyclic gadolinium-based imaging agent comprises:

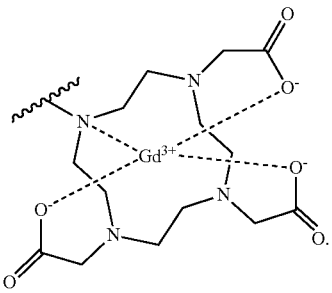

6. The liposomal composition of claim 1, wherein the macrocyclic gadolinium-based imaging agent is selected from the group consisting of:

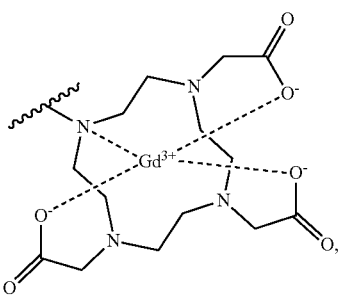

,

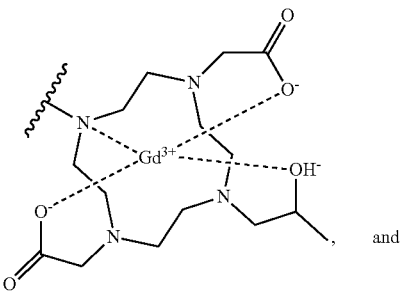

, and

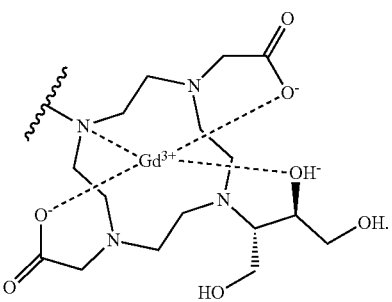

.

7. The liposomal composition of claim 5, wherein the macrocyclic gadolinium-based imaging agent is conjugated to a fourth phospholipid to comprise:

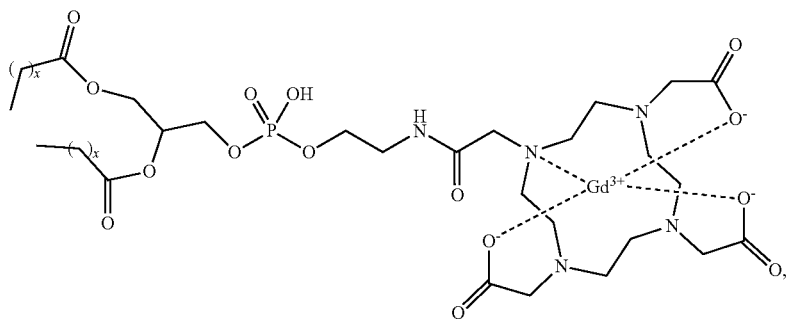

or a salt thereof, and wherein the variable x is one of: 12, 13, 14, 15, 16, 17, or 18.

8. The liposomal composition of claim 7, wherein the variable x is 16 (the conjugate: "Gd(III)-DOTA-DSPE").

9. The liposomal composition of claim 1, wherein the targeting ligand comprises:

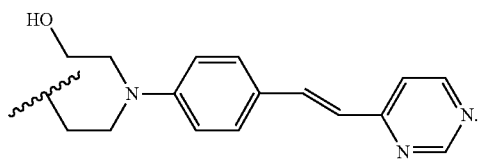 [SMILES: *CCN(CCO)c1ccc(/C=C/c2ccncn2)cc1]

10. The liposomal composition of claim 1, wherein the conjugate of the third phospholipid, the second polymer, and the targeting ligand comprises:

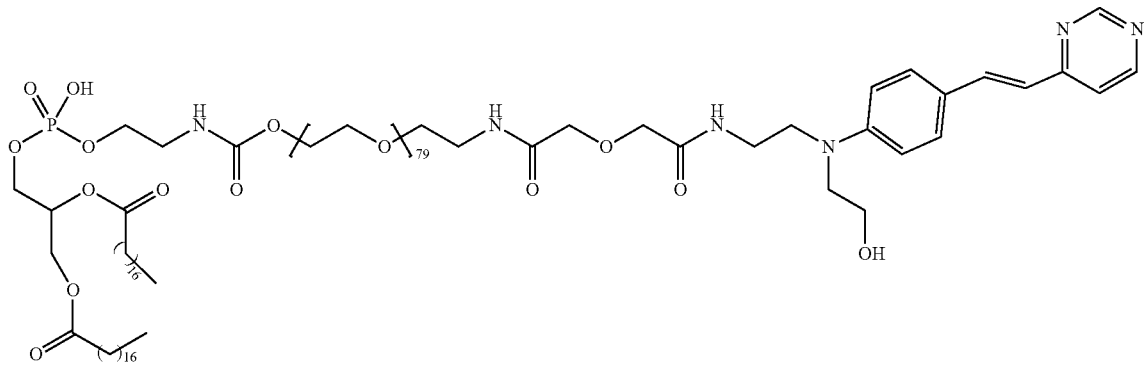

("ET3-73").

11. A liposomal composition, comprising: a macrocyclic gadolinium-based imaging agent conjugated to a first phospholipid comprising:

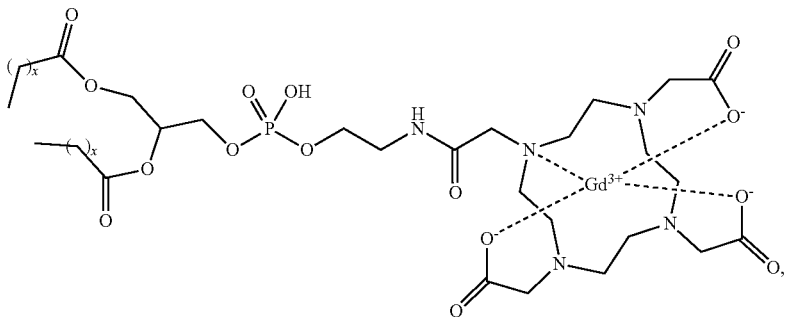

or a salt thereof, and wherein the variable x is one of: 12, 13, 14, 15, 16, 17, or 18; and a second phospholipid that is derivatized with a polymer, the polymer being conjugated to a targeting ligand, the conjugate of the second phospholipid, the polymer, and the targeting ligand comprising: is HSPC:Chol:DSPE-mPEG2000:Gd(III)-DOTA-DSPE:ET3-73=about 31.5: about 40:about 2.5:about 25:about 1.

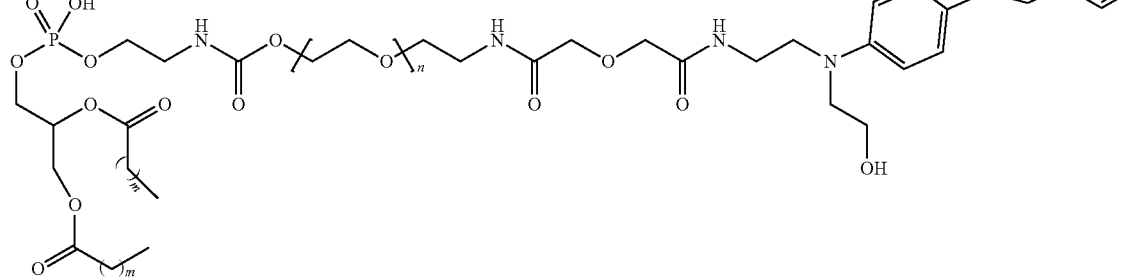

or a salt thereof, wherein the variable n is any integer from about 70 to about 90, and wherein the variable m is one of: 12, 13, 14, 15, 16, 17, or 18.

12. A liposomal composition, comprising:
liposomes, the liposomes comprising;
HSPC;
Chol;
DSPE-mPEG2000;
Gd(III)-DOTA-DSPE; and
ET3-73.

13. The liposomal composition of claim 12, wherein a molar ratio (%) of components in the liposomal composition 14. The liposomal composition of claim 12, wherein a molar ratio (%) of components in the liposomal composition is HSPC:Chol:DSPE-mPEG2000:Gd(III)-DOTA-DSPE:ET3-73=about 32.5:about 40:about 2:about 25:about 0.5.

15. The liposomal composition of claim 12, wherein the average diameter ($D_{50}$) of the liposomes in the liposomal composition is between about 100 nm to about 140 nm.

16. The liposomal composition of claim 12, wherein the liposomal composition has a pH of between 6.4 and 8.4.

17. The liposomal composition of claim 12, comprising a free gadolinium content of less than 2.5 µg/mL.

18. The liposomal composition of claim 12, wherein the liposomes have an osmolality of between 200-400 mOsmol/kg.

* * * * *